US005807671A

United States Patent [19]

Soreq et al.

[11] Patent Number: 5,807,671

[45] Date of Patent: Sep. 15, 1998

[54] METHOD OF SCREENING FOR GENETIC PREDISPOSITION TO ANTICHOLINESTERASE THERAPY

[75] Inventors: Hermona Soreq, Rishon le Zion; Haim Zakut, Savyon, both of Israel

[73] Assignee: Yissum Research Development Company of Hebrew University of Jerusalem, Jerusalem, Israel

[21] Appl. No.: 370,204

[22] Filed: Jan. 9, 1995

[51] Int. Cl.[6] .................................................... G01N 33/53

[52] U.S. Cl. ................................ 435/6; 435/7.1; 435/19; 436/518

[58] Field of Search ............................ 435/4, 6, 7.1, 19, 435/975; 436/518

[56] References Cited

PUBLICATIONS

Itoh et al, Climica Chimica Acta, 207:1178, 1992.

Aldridge (1975) "Survey of Major points of interest about reactions of cholinesterases", *Croatia Chemica Acta* 47:225–233.

Arpagaus et al. (1990) "Structure of the gene for human butyrylcholinesterase: evidence for a single copy", *Biochemistry* 29:124–131.

Ashani et al. (1991) "Butyrylcholinesterase and acetylcholinesterase prophylaxis against soman poisoning in mice" *Biochem. Pharmacol.* 41:37–41.

Balasubramanian and Bhanumathy (1993) "Noncholinergic functions of cholinesterases", *FASEB, J.* 7:1354–1358.

Carmichael (1994) "The toxins of cyanobacteria", *Sci. Amer.* 270:64–72.

Doctor et al. (1991) "Enzymes as pretreatment drugs for organophosphate toxicity", *Neurosci. Behav. Reviews* 15:123–128.

Ehrlich et al. (1994a) "Population diversity and distinct haplotype frequencies associated with ACHE and BCHE genes of Israeli Jews from Trans–Caucasian Georgia and from Europe", *Genomics* 22:268–295.

Ehrlich et al. (1994b) "Use of partially phosphorothioated antisense oligodeoxynucleotides for sequence–dependent modulaton of hematopoiesis", *Antisense Res. and Dev.* 4:173–183.

Enz and Boddeke (1991) "Pharmacologic and clinicopharmacologic properties of SDZ ENA 713, a centrally selective acetylcholinesterase inhibitor", *Ann, NY Acad. Sci.* 640:272–275.

Enz et al. (1993) "Brain selective inhibition of acetylcholinesterase: a novel approach to therapy for Alzheimer's disease", in *Progress in Brain Research* 98:431–437.

Gavageran (1994) "NiH panel rejects Persian Gulf Syndrome", *Nature* 369:8.

Glikson et al. (1991) "The influence of pyridostigmine administration on human neuromuscular function", *Fund. Appl. Toxico.* 16:288–298.

Gnatt et al. (1990) "Expression of alternatively terminated unusual human butyrylcholinesterase messenger RNA transcripts, mapping to chromosome 3q26–ter, in nervous system tumors" *Cancer Res.* 50:1983–1987.

Gnatt et al. (1991) "Human acetylcholinesterase and butyrylcholinesterase are encoded by two distinct genes", *Cell Mol. Neurobiol.* 11(1):91–104.

Gnatt et al. (1994) "Site–directed mutagenesis of active site residues reveals plasticity of human butyrylcholinesterase in substrate and inhibitor interactions", *J. Neurochem.* 62:749–755.

Goonetilleke et al. (1994) "Motor neurone disease", *Essays Biochem.* 28:27–45.

Hackley, Jr. et al. (1955) "Acceleration of the hydrolysis of organic fluorophosphates and fluorophosphonates with hydroxyamic acids", *J. Am. Chem. Soc.* 77:3651–3653.

Harel et al. (1992) "Conversion of acetylcholinesterase to butyrylcholinesterase: modeling and mutagenesis" *Proc. Natl. Acad. Sci. U.S.A.* 89:10827–10831.

Harel et al. (1993) "Quaternary ligand binding to aromatic residues in active–site gorge of acetylcholinesterase", *Proc. Natl. Acad. Sci.* 90:9031–9035.

Karlsson et al. (1985) "Anticholinesterase toxins" *Pharmacol. Ther.* 30:259–276.

Karpel et al. (1994a) "Expression of three alternative acetylcholinesterase messenger RNAs in human tumor cell lines of different tissue origins", *Exp. Cell Res.* 210:268–277.

Karpel et al. (1994b) "Overexpression of acetylcholinesterase variants induces motphogenic changes in rat glioma cells", *J. Neurochem.* 63 (Suppl 1):S63D.

Knapp et al. (1994) "30–week randomized controlled trial of high–dose tacrine in patients with Alzheimer's disease", *J. Am. Med. Assn.* 271:985–991.

Lapidot–Lifson (1992) "Cloning and antisense oligodeoxynucleotide inhibition of a human $cdc_2$ homologue required in hematopoiesis", *Proc. Natl. Acad. Sci.* USA 89:579–583.

Lev–Lehman et al. (1994) Antisense inhibition of acetylcholinesterase gene expression causes transient hematopoietic alterations in vivo, *Gene Therapy* 1:127:135.

Lockridge (1990) "Genetic variants of human serum cholinesterase influence metabolism of the muscle relaxant succinylcholine", *Pharmacol. Ther.* 47:35–60.

Lockridge (1980) "Hydrolysis of diacetylmorphine (heroin) by human serum cholinesterase", *J. Pharmac. Exp. Ther,* 215:1–8.

(List continued on next page.)

*Primary Examiner*—Paula K. Hutzell
*Assistant Examiner*—Patricia A. Duffy
*Attorney, Agent, or Firm*—Kohn & Associates

[57] ABSTRACT

A method of screening for a genetic predisposition to anticholinesterase exposure. The method includes the steps of obtaining a peripheral blood sample, and then analysing serum from the blood sample for BuChE levels and inhibitor-susceptibilites. The DNA of peripheral white blood cells from the blood sample is also screened for the presence of BuChE alleles thereby identifying patients who have a genetic predisposition to anticholinesterase exposure.

2 Claims, 12 Drawing Sheets

PUBLICATIONS

Loewenstein et al. (1993a) "Chimeric human cholinesterase: identification of interaction sites responsible for sensitivity to acetyl–or butyrylcholinesterase–specific ligands", *J. Mol. Biol.* 234:289–296.

Loewenstein (1993b) "Molecular dissection of cholinesterase domains responsible for carbamate toxicity", *Chemical–Biological Interactions* 87:209–216.

Malinger et al. (1989) "Cholinoceptive properties of human primordial, preantral, and antral oocytes: In Situ hybridization and biochemical evidence for expression of cholinesterase genes", *J. Mol. Neurosci.* 1:77–84.

Marrs (1993) "Organophosphate poisoning", *Pharmac. Ther.* 58:51–66.

Massoulie et al. (1993) "Polymorphism of Cholinesterases: A Single Gene Generates Multipe Forms . . . " *Prog. Neurobiol.* 41:31–91.

Neville et al. (1990a) "Aspartate–70 to glycine substitution confers resistance to naturally occurring and synthetic anionic–site ligands on in–ovo produced human butyrylcholinesterase", *J. Neurosci. Res.* 27;452–460.

Neville et al. (1990b) "Anionic site interactions in human butyrylcholinesterase disrupted by two single point mutations", *J. Biol. Chem.* 265;20735–20738.

Ordentilch et al. (1993a) "Dissection of the human acetylcholinesterase active center determinants of substrate specificity", *J. Biol. Chem.* 268:17083–17095.

Ordentlich et al. (1993b) "Engineering resistance to 'aging' of phosphylated human acetylcholinesterase: role of hydrogen bond network in the active center", *FEBS Lett.* 334:215–220.

Prody et al. (1987) "Isolation and characterization of full–length cDNA clones coding for cholinesterase from fetal human tissues", *Proc. Natl. Acad. Sci.* U.S.A. 84:3555–3559.

Prody et al. (1989) "De novo amplification with a 'silent' human cholinesterase gene in a family subjected to prolonged exposure to organophosphorous insecticides", *Proc. Natl. Acad. Sci.* U.S.A. 86:690–694.

Rakonczay and Brimijoin (1988) "Biochemistry and pathophysiology of the molecular forms of cholinesterases. In: Subcellular Biochemistry", *Immunological Aspects,* 12:355–378 (Plenum Press, NY).

Raveh et al. (1993) "Human butyrylcholinesterase as a general prophylactic antidote for nerve agent toxicity; in vitro and in vivo quantitative characterization" *Biochem. Pharmacol.* 45:2465–2474.

Rosenberry (1975) "Acetylcholinesterase", *Adv. Enzymol.* 43:104–210.

Seidman et al. (1994) "Overexpressed monomeric human acetylcholinesterase induces subtle ultrastructural modifications in developing neuromuscular junctions of *Xenopus laevis* embryos", *J. Neurochem.* 62:1670–1681.

Silman and Futerman (1987) "Modes of attachment of acetylcholinesterase to the surface membrane", *Eur. J. Biochem.* 170:11–22.

Soreq et al. (1990) "Molecular cloning and construction of the coding region for human acetylcholinesterase reveals a G+C–rich attenuating structure", *Proc. Natl. Acad. Sci,* U.S.A. 87:9688–9692.

Soreq et al. (1992) "Excavations into the active–site gorge of cholinesterases", *Trends Biochem. Sci.* 17:353–358.

Soreq et al. (1994) "Antisense oligonucleotide inhibition of acetylcholinesterase gene expression induces progenitor cell expansion and suppresses hematopoietic apoptosis ex vivo", *Proc. Natl. Acad. Sci.* U.S.A.

Sussman et al. (1992) "Three dimensional structure of acetylcholinesterase", in: *Multidisciplinary Approaches to Cholinesterase Functions,* Eilat, Israel, 6–10 Apr. 1992, pp. 95–108 (Plenum Press, New York).

Taylor (1991) "The cholinesterases", *J. Biol. Chem.* 266:4025–4028.

Taylor and Radic (1994) "The cholinesterases: from genes to proteins", *Annu. Rev. Pharmacol. Toxicol.* 43:281–320.

Turner (1994) "PIG–tailed membrane proteins" *Essays Biochem.* 28:113–127.

Valentino et al. (1981) "Prediction of drug sensitivity in individuals with atypical cholinesterase based on in vitro biochemical studies" *Biochem, Pharmacol.* 30:1643–1649.

Vellom et al. (1993) "Amino acid residues controlling acetylcholinesterase and butyrylcholinesterase specificity" *Biochemistry* 32:12–17.

Wang et al. (1967) "Oxime reactivation of diethylphosphoryl human serum cholinesterase", *J. Biol. Chem.* 242;2683–2687.

Willems et al. (1993) "Cholinesterase reactivation in organophosphorus poisoned patients depends on the plasma concentrations of the oxime pralidoxime methylsulphate and of the organophosphate" Arch. Toxicol. 67:79–84.

Wilson (1954) "The mechanism of enzyme hydrolysis studied with acetylcholinesterase", in *The Mechanism of Enzyme Catalysis,* pp. 642–657. (The Johns Hopkins Press, Baltimore, MD).

Winker (1994) "Tacrine for Alzheimer's disease; which patient, what dose?" *J. Am. Med. Assn.* 271:1023–1024.

Zakut et al. (1985) "Polymorphism of acetylcholinesterase in discrete regions of the developing human fetal brain", *J. Neurochem.* 45:382–389.

Zakut et al. (1990) "Acetylcholinesterase and buytrylcholinesterase genes coamplify in primary ovarin carcinomas", *J. Clin. Invest.* 86:900–908.

Zakut et al. (1992), "In vivo gene amplification in non–cancerous cells: Cholinesterase genes and oncogenes amplify in thrombocytopenia associated with Lupus Erythematosus" *Mutation Res.* 276:275–284.

Kamban et al., "Inhibition of pseudocholinesterase activity protects from cocaine–induced cardiorespiratory toxicity in rats" *J. Lab. Clin Med.,* 119:553–556 (1992).

Simone et al., "Acetylcholinesterase and butyrylcholinesterase activity in human term placenta . . . " *J. Lab. Clin. Med.,* 123:400–406 (1994).

Atack et al., "Molecular forms of acetylcholinesterase and butyrylcholinesterase in the aged human . . . " *J. Neurochem.,* 47:263–277 (1986).

Brown et al., "Pesticide exposures and other agricultural risk factors for leukemia among men in Iowa and Minnesota" *Cancer Res.* 50:6585–6591 (1990).

Coleman et al., "Interaction of a benzomorphan opiate with acetylcholinesterase and the nicotinic . . . " *Mol. Pharm.* 32:456–462 (1987).

Davis et al., "Therapeutic intervention in dementia" *Crit. Rev. Neurobiol.,* 7:41–83 (1993).

Dretchen et al., "Protection against cocaine toxicity by human buytrylcholinesterase (BCHE) in rats" *FASEB J.,* 6:A1282 (1992).

Eckstein et al., "Nucleoside phosphorothioates" *Ann. Rev. Biochem.,* 54:367–402 (1985).

Gatley, "Activities of the enantiomers of cocaine and some related compounds as substrates and inhibitors . . . " *Biochem. Pharmacol.* 41:1249–1254 (1991).

Graybiel and Ragsdale, "Pseudocholinesterase staining in the primary visual pathway . . . " *Nature,* 299:439–442 (1982).

Kambam et al., "The effects of inhibition of plasma cholinesterase and hepatic microsomal enzyme acitivity on cocaine . . . " *J. Lab. Clin. Med.,* 120:323–328 (1993).

Layer, "Cholinesterases during development of the avian nervous system" *Cell. Mole. Neurobiol.,* 11:7–33 (1991).

Layer et al., "Cholinesterases regulate neurite growth of chick nerve cells in vitro . . . " *Cell Tissue Res.,* 273:219–226 (1993).

Liao et al., "Monoclonal antibodies against brain acetyl–cholinesterases which recognize the subunits . . . " *Eur. J. Biochem.,* 215:333–340 (1993).

Marchot et al., "Binding of 125I–Fasciculin to rat brain acetylcholinesterase" *J. Biol. Chem.* 268:12458–12567 (1993).

Methia et al., Oligodeoxynucleotides antisense to the proto–oncogene c–mpl specifically inhibit . . . *Blood,* 82:1395–1401 (1993).

Olianas et al., "The muscarinic receptor adenylate cyclase complex of rat striatum . . . " *J. Neurorchem.,* 42:439–1443 (1984).

Ott and Lannon, "Exacerbation of parkinsonism by tacrine" *Clin. Neuropharmacol.,* 15:322–325 (1992).

Stein and Cheng, "Antisense oligonucleotides as therapeutic agents —is the bullet really magical?" *Science,* 261:1004–1012 (1993).

Wills, Toxicity of anticholinesterases and treatment of poisoning. in *Anticholinesterase Agents, Intl' Encyclopedia of Pharmacology*. . . Section 10, pp. 357–369 Karczmar, c (ed) Pergamon Press Oxford (1970).

Loewerstein et al., Fast inhibition rates of normal BuChE as compared AChE and the D70G "atypical". . . *10th ESN Meeting,* Jerusalem, Israel, S6 (abstract).

Neville et al., "Intramolecular relationships in cholinesterases revealed by oocyte expression of site–directed . . . " *The EMBO Journal,* vol. 11, No. 4, pp. 1641–1649 (1992).

Patinkin et al., "Manipulations of cholinesterase gene expression modulate murine megakaryocytopoiesis in vitro" *Molecular and Cellular Biol.,* vol. 10, No. 11, pp. 6046–6050 (1990).

Soreq et al., "Molecular cloning and construction of the coding region for human acetylcholinesterase reveals a G+C . . . " *Proc. Natl. Acad. Sci. USA,* vol. 87, pp. 9688–9692 (1990).

Fig-2A
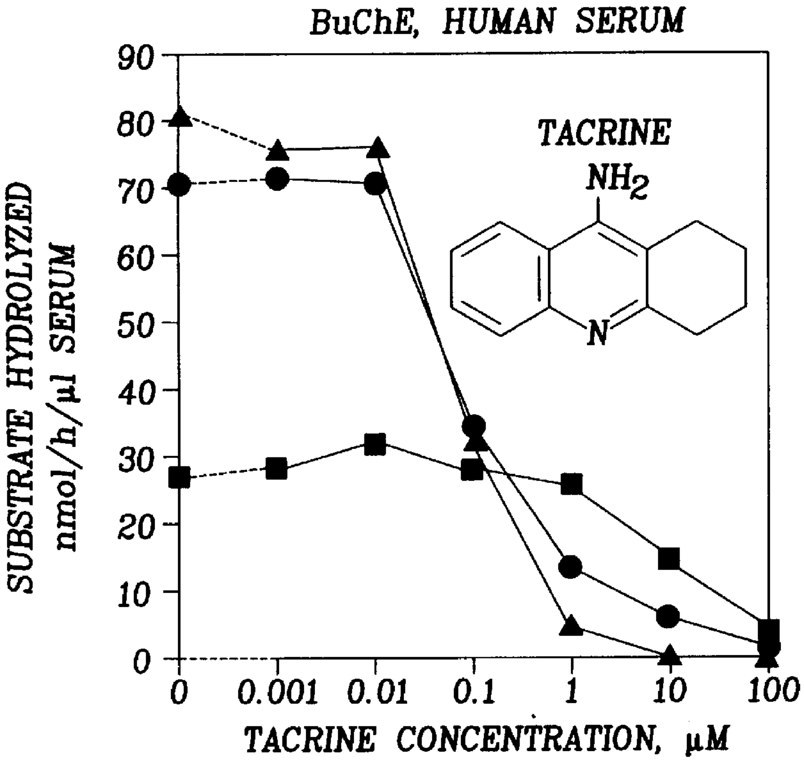
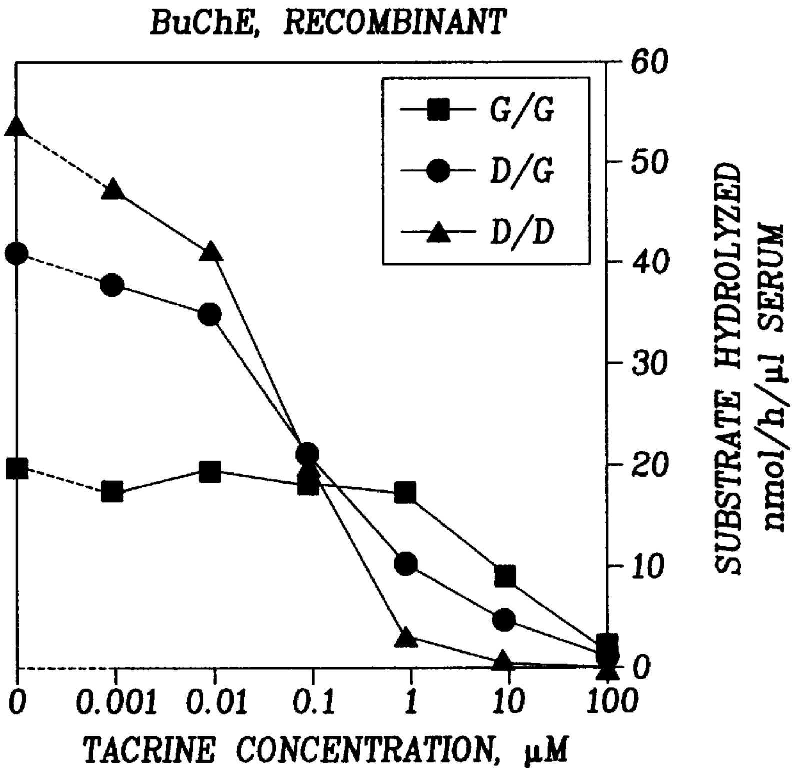
Fig-2B

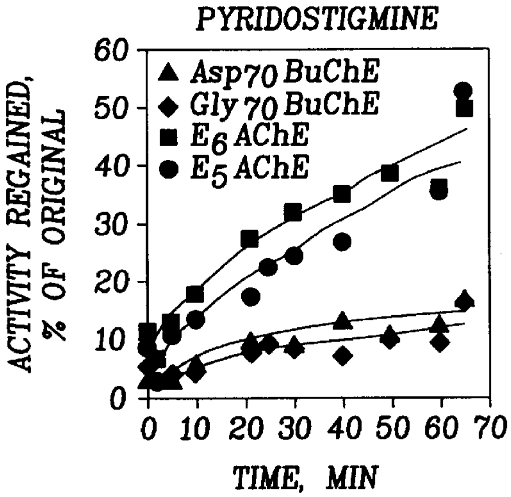

Fig-4A

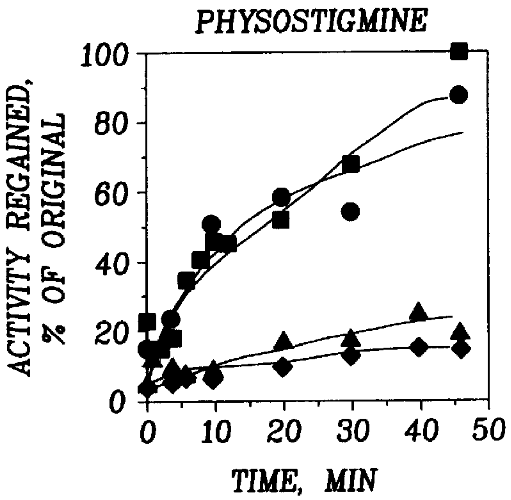

Fig-4B

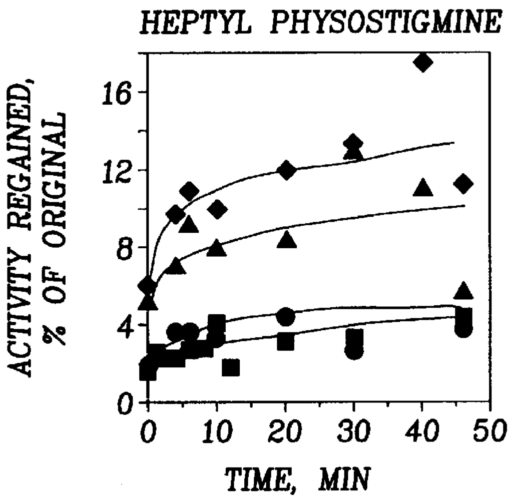

Fig-4C

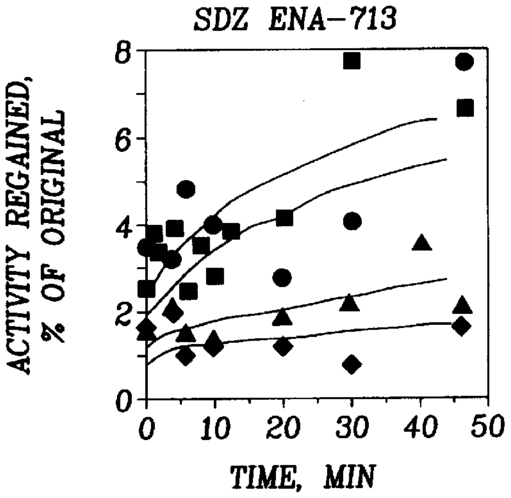

Fig-4D

CATALYSIS $$ChO\text{-}OCR + EnzOH \longrightarrow EnzO\text{-}OCR + ChOH$$

$$EnzO\text{-}OCR + OH^- \longrightarrow {}^-OOCR + EnzOH$$

ANALOGOUS REACTIONS $$XPO(OR')_2 + EnzOH \xrightarrow{k_i} EnzOPO(OR')_2 + HX$$

$$EnzOPO(OR')_2 + B: \underset{}{\overset{K_d}{\rightleftharpoons}} EnzOPO(OR')_2 \cdots B:$$

$$EnzOPO(OR')_2 \cdots B: \overset{k_r}{\rightleftharpoons} B\text{-}PO(OR')_2 + EnzOH$$

Fig-5A

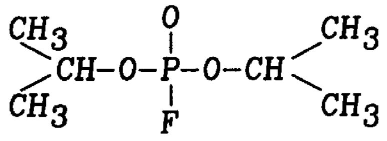
DFP
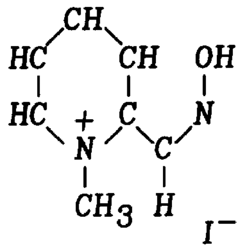
PAM
Fig-5B
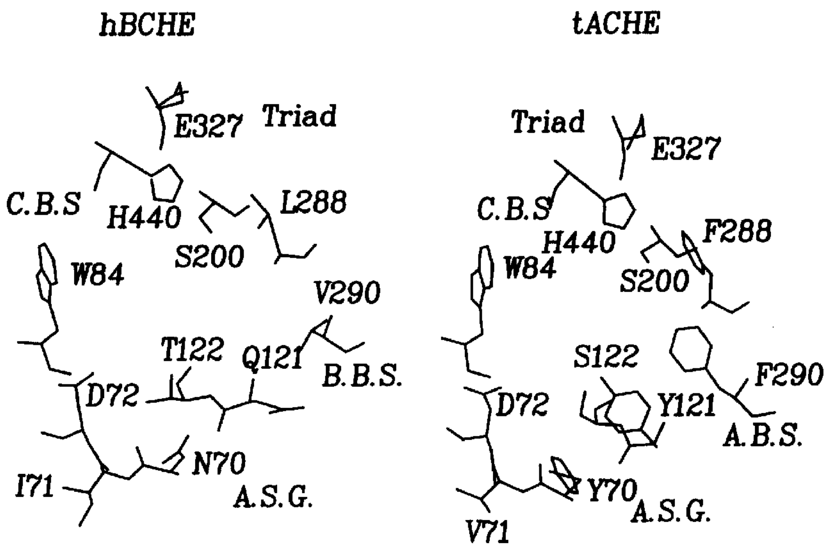
Fig-6
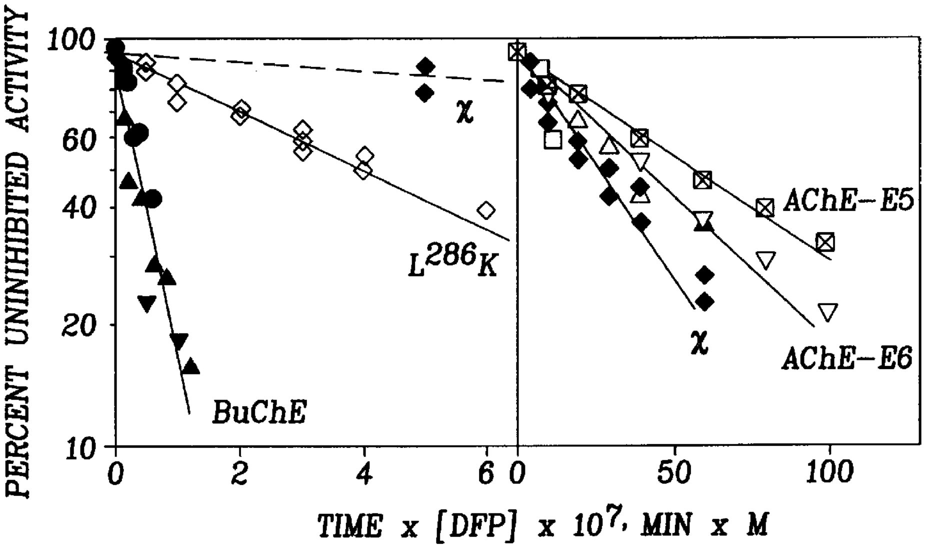
Fig-7A

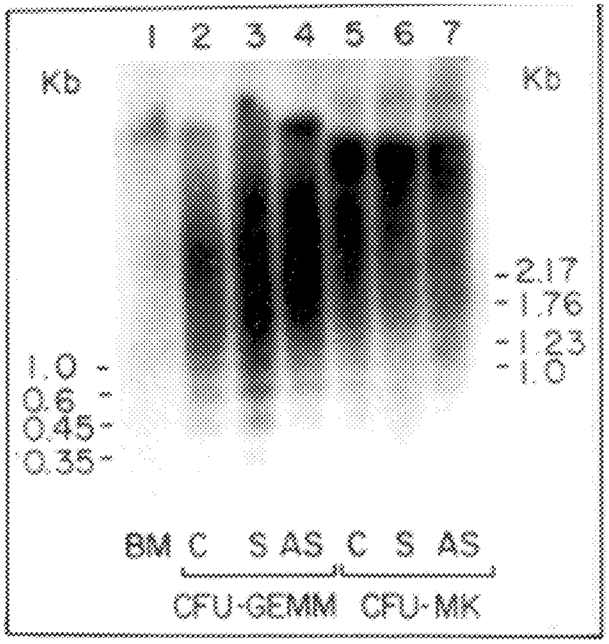
Fig—10

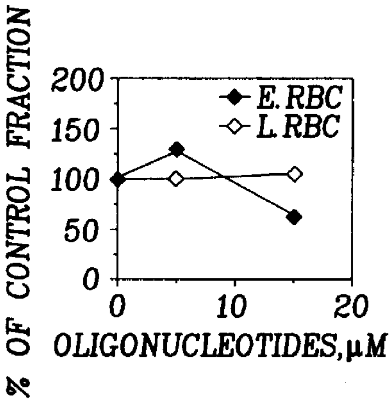
Fig–12C
Fig–13B
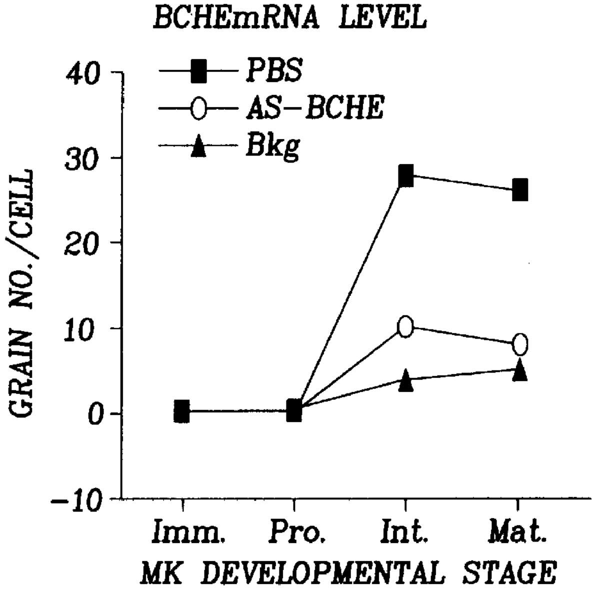
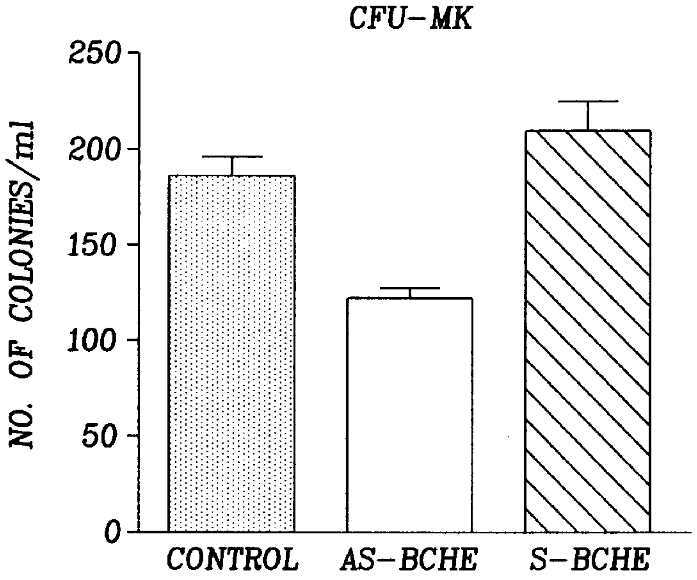
Fig–13C

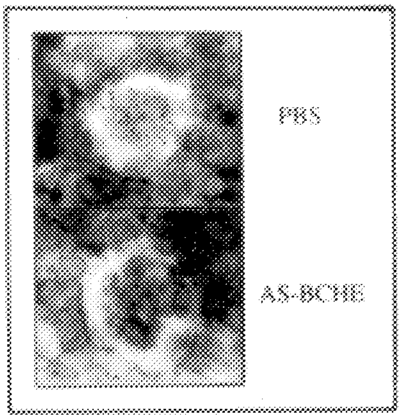
Fig—13A

METHOD OF SCREENING FOR GENETIC PREDISPOSITION TO ANTICHOLINESTERASE THERAPY

The U.S. Government has a nonexclusive, nontransferable, irrevocable paid-up license to practice or have practiced this invention for or on its behalf as provided for by the terms of Contract DAMD17-86-C-6010 awarded by the U.S. Department of the Army.

BACKGROUND OF THE INVENTION

1. Technical Field

The present invention relates to a method for screening for a genetic predisposition for adverse responses to anti-cholinesterase therapy.

2. Background Art

The clinical uses of anticholinesterases (anti-ChEs) have recently been extended in two major developments, involving many new subjects. First, during the 1991 Gulf War, the carbamate, pyridostigmine was administered prophylactically to over 400,000 soldiers, with the intention of transiently blocking (and thus protecting) a fraction of their nervous system acetylcholinesterase (AChE, EC 3.1.1.7), in anticipation of nerve agent attacks (Gavageran, 1994; Ember, 1994). Yet more recently, the reversible cholinesterase (ChE) inhibitor, tetrahydroamino acridine (THA, tacrine, Cognex®) was approved for use in patients with Alzheimer's disease, for the purpose of enhancing the availability of acetylcholine at synapses and improving residual cholinergic neurotransmission in patients suffering from massive degeneration of cholinergic neurons (Knapp et al., 1994).

Adverse symptoms were reported in both groups (Ember, 1994; Gavageran, 1994; Winker, 1994), including responses characteristic of cholinergic deficits, such as depression, general fatigue, insomnia and weight loss. However, these were only a few out of many symptoms in a complex and diverse list, the interpretation of which was complicated by incomplete medical records and the stressful situation experienced by the first group and the generally bad condition of the aging patients from the second group.

To identify the molecular basis of these adverse responses to anti-ChEs, applicants have focused on the protein targets of these agents. Most anti-ChEs were designed as selective AChE inhibitors; however, many, if not all of these drugs also interact quite efficiently with the closely related serum butyrylcholinesterase (BuChE). In fact, some consider one of BuChE's biological roles to be a scavenger of natural anti-ChEs. No allelic variant with modified biochemical properties is known for AChE, perhaps because the fully active enzyme is absolutely essential to ensure good quality cholinergic neurotransmission. In contrast, there are over 20 different allelic variants of BuChE, some of which display altered interactions with certain inhibitors (Neville et al., 1990a; Gnatt et al. 1994). This raised the possibility of a genetic basis, rooted in the polymorphism of BuChE, of the adverse symptoms experienced by some patients undergoing anti-ChE therapy.

Acetylcholinesterase (EC 3.1.1.7; AChE) and butyrylcholinesterase (EC 3.1.1.8; BuChE) are two closely homologous proteins. Both are present in all vertebrates, and both are capable of hydrolyzing the neurotransmitter, acetylcholine (ACh). Reviews, by Taylor (1991), Massoulie et al. (1993), Soreq and Zakut (1993), and Taylor and Radic (1994) contain specialized information on sub-topics, especially on cholinesterases (ChEs) of non-human species and on the cell biology aspects of these enzymes.

The most obvious and best studied function of AChE is the hydrolysis of ACh to terminate neurotransmission at the neuromuscular junction and nicotinic or muscarinic brain synapses and secretary organs of various sorts. AChE is characterized by a narrow specificity for ACh and certain inhibitors and by substrate inhibition. In humans, AChE is produced in muscle and nerve, in hemopoietic cells (Patinkin et al., 1990; Lev-Lehman et al., 1994; Soreq et al., 1994), embryonic tissues (Zakut et al., 1985; Zakut et al., 1990), several tumors (Lapidot-Lifson et al., 1989) and germ cells (Malinger et al., 1989).

The role of BuChE, beyond hydrolyzing ACh at concentrations that would cause inhibition of AChE (Augustinsson, 1948), has not been identified with certainty, but as it has a wider substrate specificity and interacts with a broader range of inhibitors, it has been proposed that it scavenges anti-ChE agents, protecting synaptic AChE from inhibition and the multitude of ACh receptors from blockade (Soreq et al., 1992).

The protein chemistry, enzymology, non-CNS/non-catalytic role(s) and genetics of AChE and BuChE has been extensively reviewed by Schwarz, et al (1995) incorporated herein by reference. Of particular interest for the present application is the following.

In man, the two functionally distinct ChEs, AChE and BuChE, which share a high degree of amino acid sequence homology (>50%), are encoded by two separate genes, ACHE and BCHE, respectively (Soreq et al., 1990). The two genes have similar exon-intron organization but radically different nucleotide composition, ACHE being G,C-rich while BCHE is A,T-rich. The presence of two distinct ChE genes in all vertebrates studied to date, indicates that both protein products are biologically required in these species, and presumably that they have distinct roles.

The human ACHE gene spans about 7 kb and includes 6 characterized exons and 4 introns. It can, through alternative splicing, give rise to several different mRNA transcripts (Sikorav et al., 1988; Maulet et al., 1990). The BCHE gene is much larger than ACHE, spanning 70 kb, and consists of 4 exons, the first of which is non-translatable but contains two potential translation initiation sites, and the second of which contains 83% of the coding sequence (Arpagaus et al., 1990; Gnatt et al., 1991). The use of fluorescent in situ hybridization with biotinylated ACHE DNA, mapped the refined position of the ACHE gene to chromosome 7q22 (Ehrlich et al., 1994a; Getman et al., 1992).

Mapping of the human BCHE gene to its defined chromosomal location, 3q26-ter, was first performed by in situ hybridization to lymphocyte chromosomes and by blot hybridization to DNA of hybrid somatic cells (Gnatt et al., 1990). Direct PCR amplification of human BCHE-specific DNA fragments from somatic cell hybrids and chromosome sorted libraries later confirmed this mapping of the BCHE gene to chromosome 3q2G-ter (Gnatt et al., 1991). When using ACHE specific primers, a prominent PCR product was observed with DNA from two different cell-lines and from one chromosome sorted library, all containing DNA from human chromosome 7.

These findings confirmed predictions that the two closely related CHE genes are not genetically linked in the human genome (Gnatt et al., 1991). They further revealed that these two apparently unrelated genes are both located at chromosomal sites subject to frequent breakage in leukemias (Ehrlich et al., 1994a).

Drugs that are Hydrolyzed or Scavenged by Cholinesterases

When a drug enters the body through the blood stream, its first encounters with a ChE are with AChE of the erythrocyte membrane outer surface and with circulating BuChE. However, since BuChE is capable of interacting with a wider range of ligands than AChE, and in some cases, at much higher rates (Schwarz et al., 1994), it appears to be the major scavenger of anti-ChE agents. Support for this can be found in the absence of a correlation between $IC_{50}$ values of AChE for a range of carbamate anti-ChE's, and their $LD_{50}$ values, while a positive correlation between these parameters exists for BuChE (Loewenstein et al., 1993b).

Succinyl choline, an inhibitor of AChE, is a commonly used muscle relaxant. BuChE recognizes succinyl choline as a substrate, and the slow hydrolysis of the agent limits the duration of its action in vivo. BuChE has been shown in vitro to hydrolyze the methyl ester bond of cocaine and its derivatives (Isenschmid et al., 1989; Gatley, 1991). In vivo, in contrast to cytochrome P-450-catalyzed destruction of cocaine, which produces hepatotoxic norcocaine nitroxide, BuChE-catalyzed hydrolysis of cocaine generates innocuous products. The serum levels of BuChE, too, as modulated by ChE inhibitors, correlate with serum levels of cocaine and related narcotics (Kambam et al., 1992) and with their physiological effects (Kambam et al., 1993). This clearly indicates a role for BuChE that must be recognized, especially by those practicing in areas or populations with narcotic usage. Furthermore, exogenous (human) BuChE has been shown to confer protection against cocaine toxicity in rats, both when given prophylactically or therapeutically (Dretchen et al., 1992). Following the elucidation of the pharmacological effects of cocaine, a series of analogs was synthesized, yielding some of the local anesthetics still in use today. As their chemistry is based on that of cocaine, not surprisingly they, too, are subject to hydrolysis and inactivation by BuChE (Baldessarini, 1990).

An aryl acylamidase activity of BuChE, which is strongly inhibited by classical cholinesterase inhibitors, has also been reported. This may have implications for the hydrolysis of analgesics such as paracetamol (Balasubramanian and Bhanumathy, 1993).

Inhibition of Cholinesterases

Inhibition of ChE can be achieved by several different mechanisms. Simple competitive inhibition is caused by such quaternary compounds as edrophonium, which binds selectively to the active site where it is stabilized by interaction of its quaternary nitrogen with the choline-binding pocket, and by hydrogen bonding (Sussman et al., 1992; Harel et al., 1993). In contrast to edrophonium, carbamyl esters serve as hemi-substrates. During catalysis, a carbamoyl enzyme intermediate is formed, which is far more stable than the acetyl-ChE intermediate. The very slow hydrolysis of the intermediate effectively sequesters ChE for several hours. Neostigmine, one of many physostigmine derivatives, has increased stability and potency equal to or greater than physostigmine. Demecarium, two neostigmine molecules linked by a 10-carbon chain, has even greater affinity. As an ACh analog, physostigmine can also block nAChRs (nicotinic acetylcholine receptor) (Shaw et al., 1985; Coleman et al., 1987). In fact, quaternary ammonium anti-ChE compounds have additional direct actions at cholinergic sites, either as agonists or antagonists. For example, neostigmine affects the spinal cord and the neuromuscular junction, both by inhibition of AChE activity and by stimulation of cholinergic receptors.

Over a hundred years ago the Western world became aware of the pharmacological properties of calabar bean extracts (Silver, 1974). These were eventually attributed to the ability of physostigmine to inhibit ChEs. Synthetic versions, neostigmine and pyridostigmine have been made in order to enhance effectiveness or specificity.

Glycoalkaloids and aglycones of the Solanaceae are also inhibitors of ChEs. The Solanaceae include such important foods as the potato, tomato and eggplant. Although both in vitro effects of these substances and cases of poisoning by them have been documented, it is not yet clear whether they exert an evolutionary pressure (Ehrlich et al., 1994a).

Organophosphates (OPs), mainly man-made but also in at least one example, occurring naturally in cyanobacteria (Carmichael, 1994), act as hemi-substrates of ChEs, specifically phosphorylating the active site serine, just as the natural substrate acylates it. Since the rate of hydrolysis of the phosphoryl or phosphonyl enzyme is very much slower than deacylation, OPs are effectively irreversible ChE inhibitors.

OP poisoning has been recently reviewed by Marrs (1993). OPs have also been developed as chemical weapon systems, and these potential battlefield threats have provoked considerable study of their short- and long-term physiological effects. OP anti-ChEs are potent insecticides, due to their inhibition of the insects' flight muscle ChE, with resulting paralysis and death. Because the OPs are environmentally non-persistent—being subject to non-enzymatic hydrolysis—they are increasingly replacing organic chloride compounds which are in disfavor because of their indiscriminate effects (WHO, 1986a,b). As a result of the extensive use of OP pesticides in agriculture, accidental poisoning of humans increased between 1973 and 1984, from half a million to one million cases per year, worldwide (United Nations Security Council, 1984). Particularly affected are locales where their use is poorly regulated.

There are immediate effects of OP poisoning, including respiratory depression, muscular paralysis and convulsions (Foutz et al., 1987), and delayed effects including diarrhea, weight loss, insomnia, myopathy and mental depression (Wecker et al., 1978). Although most modern insecticides are designed to have low vertebrate toxicity, subacute dietary consumption of these poisons (contaminating remnants on vegetables and fruits) may induce chronic cholinergic poisoning of fish and animals (Salte et al., 1987), including humans (Ratner et al., 1983). One very serious effect of exposure to OPs is the increased risk of leukemia (Brown et al., 1990). A molecular description of some secondary effects of OP poisoning on the nervous system has been proposed: the down-regulation of muscarinic receptors following chronic inhibition of AChE (Olianas et al., 1984; Clement, 1991).

Neurodegenerative Diseases Related to Cholinergic Malfunction

Defective cholinergic signaling has been found in a number of neurodegenerative disorders in which pathological changes in the levels of AChE and BuChE as well as CHAT (choline-acetyltransferase) and AChR are observed (Rakonczay and Brimijoin, 1988). As these symptoms are organ-specific, rather than global, they may indicate a failure of normal tissue-specific post-transcriptional (alternative splicing) or post-translational modifications. The following is a parital list of these diseases and the type of anticholinesterase therapy that is used as well as the response. More detailed descriptions of the diseases are included herein below as necessary and summarized in Schwartz et al (1995).

1. Alzheimer's Disease (AD) is the most common type of adult-onset dementia. The general malfunction of the cholinergic regions of the brain invariably leads to death. The severity of the disease parallels the reduction in levels of ACHE and CHAT in the frontal and temporal cortices (Perry et al., 1978). A diminished number of cholinergic neurons in basal forebrain nuclei and decreased ACh production in the brain of AD patients, are thought to cause some of the characteristic cognitive impairments. In the affected brain regions, the decrease of AChE is most pronounced in the G4 form (tetrameric globular form; Atack et al., 1983). This loss is accompanied by an increase in BuChE (Atack et al., 1986) and is correlated with selective degeneration of the presynaptic structures (De Kosky and Scheff, 1990). It has been suggested that anti-cholinergic drugs impair the memory of healthy individuals in a manner parallel to that observed early in the development of AD. Therefore, the principal current AD therapeutic approach, and the most promising one in the short term, is the stimulation of the cholinergic system. Precursor loading, with choline or phosphatidyl choline, is ineffective. However, the anti-ChE agent, physostigmine, has been shown to have a small, short-term positive effect on cognitive functions (Davis et al., 1993 and papers therein cited). More recently developed compounds, like SDZ ENA 713 (Sandoz), have greater central selectivity and longer duration of action than physostigmine (Enz et al., 1993) and is thought to bind specifically to the Gl form of AChE, presumed to be the form involved in postsynaptic ACh hydrolysis (Marquis and Fishman, 1985). Its action is concluded to be on the CNS because of its ability to increase the frequency of rapid eye movements during REM sleep (Enz et al. 1991). Nevertheless, higher doses of the drug caused a transient drop in serum BuChE activity, indicating that it inhibits BuChE as well as AChE.

The first anti-ChE drug to be approved for use in AD therapy in the USA is Cognex® (Parke-Davis, 1,2,3,4-tetrahydro-9 aminoacridine, THA, tacrine). Recently, there has been a report of a multi-center, double-blind, placebo-controlled trial of THA therapy, which included 663 patients suffering from mild to moderate AD. It was shown that THA produced statistically significant, dose-related improvements. However, after 30 weeks, significant data were available from only 263 patients. The primary reason for withdrawal of patients from the study was asymptomatic hepatotoxicity, as revealed by elevated serum levels of alanine aminotransferase. The susceptibility to THA was highly variable, the level of the aminotransferase usually being less than three times the upper limit of normal value, but in 2% of the cases it reached 20 times the upper limit of normal, prima facia evidence of hepatocellular necrosis. The adverse effects were rapidly reversed when treatment was terminated, and the majority of patients were able to return to the study with lower dosages of THA (Knapp et al., 1994; Watkins et al., 1994).

The practical benefits of THA therapy have, however, been questioned. It is argued that the improvement of cognitive function in AD patients receiving THA was superficial; the underlying deterioration continued unabated, as became evident when THA therapy was discontinued. Moreover, severe cholinergic side-effects were observed in a significant number (over 10%) of THA treated patients. Finally, only patients suffering from mild to moderate AD respond to THA treatment, while more severe cases do not benefit from this therapy (Winker, 1994). A smaller study (Minthon et al., 1993) has made similar findings.

2. Parkinson's Disease (PD) is a common type of adult-onset chronic degenerative disorder of the CNS. Since PD is associated mainly with the dopaminergic, and not with the cholinergic system, few characterizations of AChE in PD have been performed. However, AChE activity has been observed in dopaminergic brain areas and decreased AChE activity and molecular form changes that parallel those found in AD have been observed in up to 30% of PD. Therefore, cholinergic signaling may be connected with neurodegenerative processes in general, or more specifically with the pathophysiology of PD (Ruberg et al., 1986). PD patients are usually treated with tricyclic anti-depressants. The anti-cholinergic side effect of these drugs may be the basis of some of the benefit shown by this treatment of PD patients. Similarly, there is evidence of worsening of the symptoms in a PD-patient receiving the anti-ChE, THA (Ott and Lannon, 1992).

3. Huntington's Disease (HD) is a dominant inherited autosomal neurodegenerative disorder with symptoms usually evident at the age of 30 to 40, and is associated with genetically programmed cell death in the CNS. The disease, progressing over a 10–20 year period, eventually destroying all motor function. In most HD cases, progressive dementia is a feature when cholinergic neurons of the brain stem are affected. AChE activity is diminished only in selective bundles of the affected area, known for their rich AChE activity and CHAT activity is decreased in these same areas.

4. Amyotrophic lateral sclerosis (ALS), or motor neuron disease, is characterized by motor neuron degeneration and progressive failure of neuromuscular transmission. Both upper and lower motor neurons are affected. In neuromuscular endplates (NMEs) significant decreases of all forms of AChE is observed. The defect is thought to be related to disassembly of the synapses and NMEs due to an excitotoxin, a failure of a trophic factor, or a failure to detoxify a xenobiotic, the consequent decrease in nerve signaling, causing a defect in AChE excretion (Goonetilleke et al., 1994).

5. Myasthenia gravis (MG) an autoimmune neuromuscular disease, characterized by muscle weakness due to autoimmune anti-nAChR antibodies is often treated with myostigmine, a synthetic physostigmine derivative. Edrophonium induces an immediate, but brief, relief of the characteristic symptoms, due to reversible binding to the active site, terminated by rapid excretion of the drug by the kidneys. There has been noted a considerable individual variation in the dosages of anti-ChE agents required to control the disorder.

6. There is ample evidence for perturbations in cholinergic functions being associated with hematological disorders. The increased risk of leukemia following exposure to OP agents has been mentioned. Down's syndrome, like familial Alzheimer's disease, is linked to chromosome 21, (Percy et al., 1993), and is associated with AChE deficiencies, and affected individuals have a high incidence of leukemia. Paroxysmal nocturnal hemoglobinuria, also associated with an elevated risk of leukemia, is characterized by a failure of the post-translational glycosylation of AChE. This prevents transport to and interaction of the enzyme with the erythrocyte membrane (Turner, 1994). Several other hematological disorders associated with the cholinergic system were described by Soreq and Zakut (1993). Recently, antisense inhibition of ACHE gene expression, using phosphorothioated oligodeoxynucleotides, has been shown to induce massive proliferation of meloid cells in bone marrow cultures, an ex vivo mimic of a leukemic syndrome (Soreq et al., 1994). This is a warning that supreme caution must be used in the development and use of anti-ChE drugs or insecticides.

Recent studies provide evidence for the idea of a developmental role for ACh (Soreq et al., 1994; Brown et al., 1990; Schwarz et al, 1995). A recent report (Layer et al., 1993) suggests a cell adhesion role for AChE. The developmental role has also been suggested for BuChE and AChE in ex vivo developing chick motor axons based on the use of selective inhibitors (Layer, 1991; Layer et al., 1988a,b, 1993). Thus, there is accumulating evidence for a developmental role (or roles) for ChEs which is not obviously related to their catalytic activity. Further experiments will be needed to determine whether this function is related to the presumed cell adhesion properties of these enzymes.

The above summary of the actions of ChEs and anti-ChEs show the critical role of cholinesterases and anti-cholinesterases. In particular, several of the reports suggest that there is an at-risk population of people who are exposed to anti-cholinesterase agents, either environmentally or as drugs, some of whom will respond well and others who have side effects as shown in the AD trials.

It would be useful to identify the sub-population who are sensitive to anti-cholinesterase drugs. Conversely, it would be useful to identify people who have a high tolerance to such drugs such that they would be at least risk in environmental exposure.

SUMMARY OF THE INVENTION

According to the present invention, a method of screening for a genetic predisposition to anticholinesterase exposure is disclosed. The method includes the steps of obtaining a peripheral blood sample from patients, and then analysing serum from the blood sample for BuChE levels and inhibitor-susceptibilites. The DNA of peripheral white blood cells from the blood sample is also screened for the presence of BuChE alleles thereby identifying patients who have a genetic predisposition to anticholinesterase exposure.

The present invention also includes a kit for screening for a genetic predisposition to anticholinesterase exposure. The kit includes hybridization probes for BuChE alleles, and reagents for determining serum BuChE levels.

The present invention further includes a method for the dissection of sequential enzyme-mediated reactions. The method includes the steps of preparing anti-enzyme antibody-coated wells of microliter plates and then partially purifying the requisite enzymes by adsorption onto the antibody-coated wells of microliter plates. Utilizing the immobilized enzyme the appropriate activity assay for analysis of the adsobed enzyme can be performed.

BRIEF DESCRIPTION OF THE DRAWINGS

Other advantages of the present invention will be readily appreciated as the same becomes better understood by reference to the following detailed description when considered in connection with the accompanying drawings wherein:

FIG. 2A–B is a pair of graphs of the inhibition of serum and recombinant BuChE by tacrine wherein symbols for serum types are as in FIG. 1 with (A) showing data for serum types inhibited by tacrine and (B) tacrine inhibition is observed on equivalent total amounts of recombinant normal (D/D), "atypical" (G/G) and a 1:1 mixture of the two (D/G);

FIG. 4 is a series of graphs showing the time-dependent spontaneous reactivation of recombinant human ChEs after complete inhibition of the immobilized enzymes followed by removal of unreacted inhibitor, inhibitors used were as in FIG. 1 and serum was $Asp_{70}$BuChE (▲), $Gly_{70}$BuChE (♦), $E_6$AChE (■), $E_5$AChE (●);

FIG. 5A–B is a schematic representation of (A) the reactions for catalysis and analogous reactions and (B) the chemical structures of DFP and PAM;

FIG. 6 is a series of schematic representation of active site environment in human BuChE and Torpedo AChE following crystal structure and numbering of residues as in Torpedo.

FIG. 7A–B is a series of graphs showing the measurement (A) of inactivation of ChEs by DFP wherein data are presented as percent original activity vs. duration of exposure to DFP times the DFP concentration ($k_i$ [DFP]) and symbols for BuChE inactivations: ■ 1 nM, ● 5 nM, ▲ 10 nM, ▼ 50 nM DFP, for AChE (E6) inactivation: □ 0.1 $\mu$M Δ 0.5 $\mu$M, ▽ 1 $\mu$M DFP, for AChE (E5) ⊠ 1 $\mu$M DFP, for $L^{286}$K BuChE inactivation: ◇ 50 nM DFP, the BuChE/AChE chimera (X) ♦ 0.5 $\mu$M DFP, is shown in both panels to assist correlation of variants with vastly different inactivation rates and (B) reactivation of DIP-BuChE by PAM wherein a logarithmic function of the regain-in-activity vs. time is presented for BuChE ■, the $L^{286}$K mutant ◇ in 1 mM PAM, for AChE (E6) ▽, AChE (E5) ⊠, and the chimera ♦, in 0.6 mM (right panel) and 1 mM PAM (left panel), data for PAM is shown in both panels to assist correlation of variants with vastly different inactivation rates;

FIG. 10 is a photograph of a slab gel electrophoresis showing partially phosphorothioated AS-BCHE does not alter apoptotic DNA fragmentation in ex-vivo cultures of hematopoietic cells, equal quantities (1 $\mu$g) of DNA from non-treated control (C) cultures or those treated with S-BCHE (S) or AS-BCHE (AS) or fresh Bone marrow DNA (BM) were electrophoresed, blotted and hybridized, autoradiographic exposure was for 1 day, molecular size markers (Boehringer/Mannheim) were electrophoresed in parallel for size calibration (righthand side) and ladder of nucleosomes (sized on the left side), reflecting apoptosis, appeared in all cultures but not in fresh bone marrow, arbitrary apoptotic index values were calculated by phosphoimage analysis (Fuji, Tokyo, Japan) of exposed plates, determining radioactive labeling of fragmented (<2 Kb) over intact DNA;

FIG. 13A–C shows duration of AS-BCHE effects in vivo in (A) a photomicrograph of in situ hybridization with almost no BCHEmRNA could be detected over MK in bone marrow smears from treated mice, (B) a graph showing labeling decrease through the MK developmental stage wherein PBS: -■-, AS-BCHE: -○- and Background: -▲-, and (C) in vivo-ex vivo effect of control (filled bar), AS- (open bar) and S-BCHE (diagonal lines) on CFU-MK colony number, colony counts were scored in three different cultures with average values and standard deviations presented.

DETAILED DESCRIPTION OF THE PREFERRED EMBODIMENT

Figure 1A:
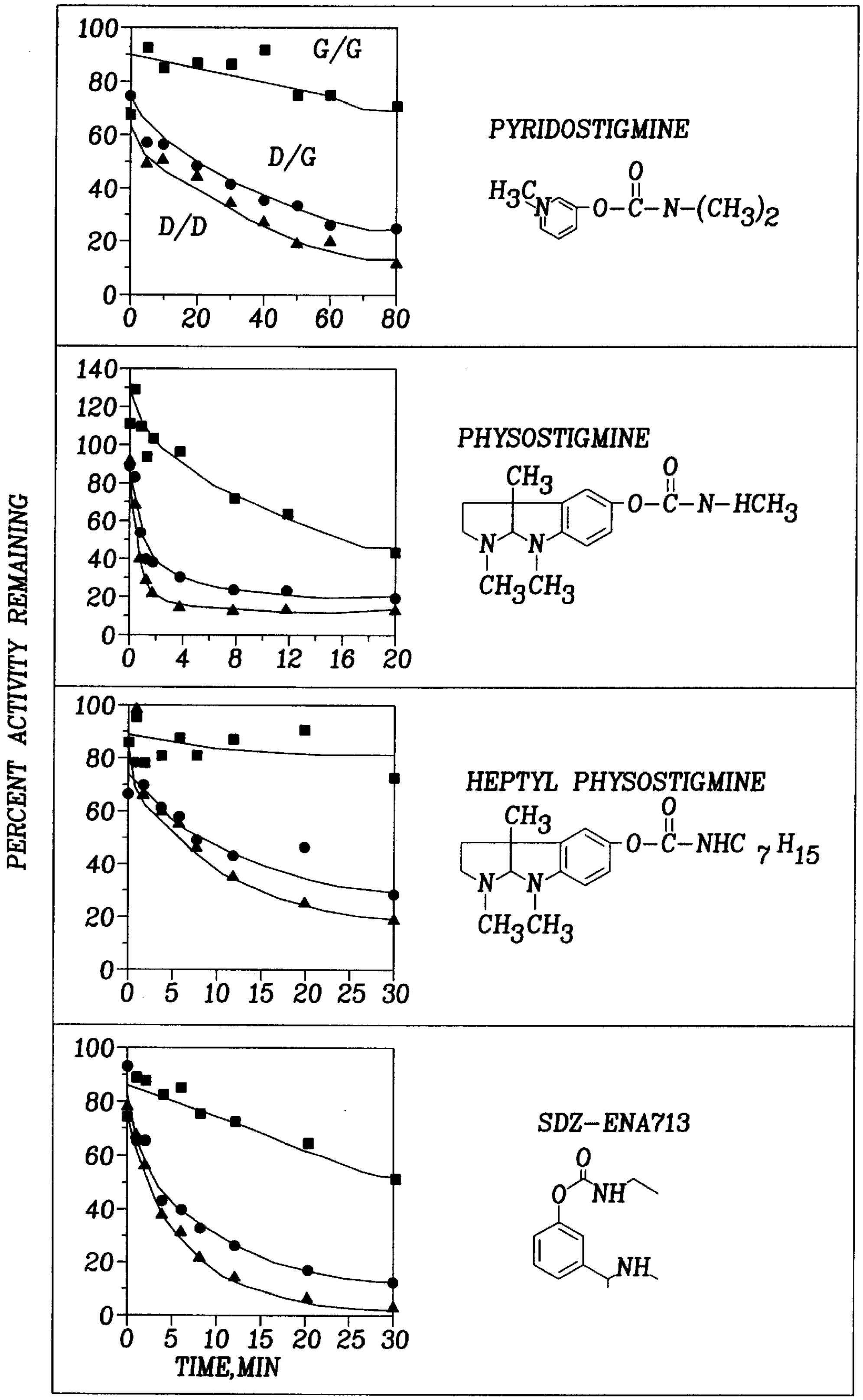
FIG. 1A–B is a series of graphs showing the inhibition of BuChE in human sera by carbamate anti-ChEs, pyridostigmine (10 $\mu$M), physostigmine (1 $\mu$M), N-heptyl physostigmine (0.01 $\mu$M) and SDZ ENA713 (10 $\mu$M) wherein panels (A) is the percent original acitivity of immobilized ChEs shown as a function of time of exposure to the four carbamates and (B) is the consumption of BuChE activity by the four carbamate inhibitors with the data of (A) used to calculate the activity lost from serum samples during incubation with each inhibitor as a function of incubation time, apparent gains of activity are rendered as zero loss, and wherein serum types are G/G (■) is a serum sample from a homozygote for the "atypical" BuChE variant, G/D (●) is a heterozygote for this variant and D/D (▲) is a normal homozygote.

The present invention provides a method of screening for a subpopulation that has a genetic predisposition to anticholinesterase exposure. The method includes the steps of first obtaining a peripheral blood sample, then analysing serum from the blood sample for BuChE levels and inhibitor-susceptibilites, and also screening DNA of peripheral white blood cells from the blood sample for presence of BuChE alleles. From the combination of these assays it is then possible to identify patients who have a genetic predisposition to anticholinesterase exposure.

The invention can be practiced wherein the the anticholinesterase exposure is by anticholinesterase drug therapy for neurodegenerative diseases or other conditions related to cholinergic malfunction. The neurodegenerative diseases or other conditions are selected from the group consisting of adult-onset dementias such as Alzheimer's disease, Parkinson's disease, Huntington's Disease, Amyotrophic lateral sclerosis or motor-neural degenerative diseases like Myasthenia Gravis. The drug therapy giving rise to anticholinesterase exposure can also be related to hematological diseases.

The anticholinesterase exposure can also result from exposure to organophosphates or carbamate insecticides. The method can also include individuals that are exposed to anticholinesterases and who are drug addicts.

In a patient who presents with what may be an adverse cholinergic symptom, the patient's peripheral blood is drawn and serum BuChE is tested against BTCh with the results compared to that of normal BuChE. Further the response to hydrolyzing succinylcholine, will also be evaluated. Responses below normal will indicate an impaired BuChE response. To determine if the impaired response is genetic, PCR amplification, informative SauIIIA restriction and direct sequencing of the corresponding region from the BCHE gene in the peripheral blood DNA by previously established techniques (Ehrlich et al., 1994a) can be undertaken to determine which BCHE alleles are present.

Routine screening of serum BuChE can be undertaken prior to administering anti-cholinesterase drugs such as tacrine. For those with impaired BuChE responses, the use of the drug would be contra-indicated. Alternatively, genetic screening of patients can be undertaken as well as those who will be at risk of exposure due to environmental agents such as pesticides. However, since not all mutations may be identified and new ones can arise, the genetic screen is most efficient in combination with screening of serum BuChE.

For the genetic screening in the preferred embodiment is PCR amplification with informative SauIIIA restriction enzyme analysis or with direct sequencing of the corresponding region from the BCHE gene in the peripheral blood DNA by previously established techniques (Ehrlich et al., 1994a). Allele-linked RFLPs may also be useful in a defined population in which there is linkage disequilibrium between specific RFLP haplotypes and variant BuChE. In family studies locus-lined RFLPs can be useful. Utilization of DNA denaturing gradient gel electrophoresis and RNase cleavage techniques taking advantage of mismatches between specific DNA or RNA probes and variant sequences.

In screening the serum BuChE the micro assay as set forth in Example 2 and briefly described herein below is used.

As part of the present invention an assay was developed in order to examine the roles of various regions in human ChEs on specific steps in the catalytic process. This analysis requires the dissection of the various steps in the process, a sequential analysis. The assay employes successive DFP phosphorylation and oxime-induced dephosphorylation as steps analogous to the acylation and deacylation reactions of substrate hydrolysis by these enzymes. Adsorption of the recombinant ChEs onto immobilised selective monoclonal antibodies enriches the enzymes, separates the catalytic steps and prevents oxime-dependent acceleration of substrate hydrolysis. The rate constants thus derived are very close to those calculated by others for the corresponding purified proteins in solution.

The assay, as set forth in the Examples herein below, which employs partial purification by adsorption (Seidman, 1994) onto antibody-coated wells of microtiter plates followed by an activity assay is suitable for screening large numbers of mutant proteins, often the rate-limiting step in a study. Also, it is adaptable to the dissection of other enzyme-mediated sequential reactions, for example, protein phosphorylation and dephosphorylation by kinases and phosphatases, or other reversible covalent modifications that modulate protein properties.

In brief this assay consists of the following steps: coating appropriate anti-ChE monoclonal antibodies in multi-well plates and then immobilizing ChEs from the serum of the patient on the antibody. By appropriate selection of monoclonal antibodies that are not directed against the active site of the enzyme, the enzymes activity can them be measured on the plate by the addition of substrate and spectrophotometric measurement of the substrate conversion.

The present invention also provides a kit for screening for a genetic predisposition to anticholinesterase exposure. The kit includes hybridization probes for BuChE alleles (Loewenstein, et al., 1993a), and reagents for determining serum BuChE levels.

The invention is based on the following observations that have lead the applicants to hypothesize and with the data from the Examples herein below determine that there are subpopulations that are genetically predisposed to respond either positively or negatively to anti-cholinesterase compounds or drugs.

1. There is a common natural mutant of BuChE, the "atypical" variant, has been identified that is unable to hydrolyze succinyl choline.

2. There are individuals who carry a variant BCHE allele, one of those that code for catalytically inactive BuChEs, and these people have an increased sensitivity to OP-poisoning (Prody et al., 1989).

3. In a case study, an individual with exceedingly low BuChE activity and a history of exposure to agricultural OPs had a 100-fold amplification of the "atypical" variant BCHE gene, which was not seen in his parents, but was passed on to the next generation (Prody et al., 1989). The clinical consequences of this are not yet apparent, but any potential effect of OPs on the genome is of great concern.

4. There has been noted a considerable individual variation in the dosages of anti-ChE agents required to control MG. This may be due to individual levels of the autoantibodies, or may be due to genetic differences in the BuChEs.

5. In AD, the susceptibility to THA was highly variable, the level of the aminotransferase usually being less than three times the upper limit of normal value, but in 2% of the cases it reached 20 times the upper limit of normal, prima facia evidence of hepatocellular necrosis. The adverse effects were rapidly reversed when treatment was terminated, and the majority of patients were able to return to the study with lower dosages of THA (Knapp et al., 1994; Watkins et al., 1994).

6. In AD, anti-ChE agents are in trial, as discussed herein above. One such agent, Tacrine, was approved in 1994. Higher doses of the drug caused a transient drop in serum BuChE activity, indicating that it inhibits BuChE as well as AChE.

These observations as well as the material following have led the applicants to determine that there are variant BuChE alleles and affect an individual's response to anti-cholinesterase compounds.

Over several decades, large-scale population surveys of BuChE phenotypes have been carried out. Tens of thousands of individuals have been screened from different continents and ethnic origins (Ehrlich et al., 1994a). Since the BCHE gene was cloned in 1986, more than twenty different naturally occurring mutations have been documented (see Table 1 in Schwarz, et al, 1995), with the great majority of the variant phenotype individuals carrying the D70G substitution. The variation was identified as a point mutation of aspartate 70, which was replaced by a glyicne residue ($D^{70}G$) (McTiernan et al., 1989; Lockridge, 1990; Neville et al., 1990b), and the variant was demonstrated to display decreased interactions with inhibitors (Gnatt et al., 1990; Neville et al., 1990a; McGuire et al., 1989) and a 4-fold lower specific activity than the wild-type BuChE (Neville et al., 1992).

The various mutated proteins result in a variety of phenotypes, including the complete absence of any BuChE protein due to premature termination of protein synthesis ("silent" mutation). In at least one area of the brain, BuChE has been demonstrated in cells other than those that have AChE, suggesting a unique function (Graybiel et al., 1981, 1982). The mere existence of a "silent" phenotype, where individuals do well in spite of having no BuChE activity, has been used to argue that BuChE has no important function. However natural selection operates on the level of species, not individuals; what may be tolerated in an isolated individual may, over time and numbers, be disadvantageous to a community. Also, "knock-out" experiments have sometimes found no phenotypes for damaged genes; it would be reckless to conclude therefore, that all such genes have no important biological role. With the exception of two polymorphisms at the 5' and 3' non-translated sequence, no mutation in BChE cDNA has yet been found that does not cause alteration in the protein sequence. Together, the catalytically silent mutations comprise 0.001% of homozygotes, which is far less than the catalytically active variants (Ehrlich et al., 1994a). Even in the absence of a well-understood physiological role for BuChE, this in itself suggests a selection advantage for carriers of various genes coding for active proteins, as compared with "silent" gene carriers.

Interestingly, the largest and main coding exon, E2, has 15 of the known mutations found on the BCHE gene. Thus, the average incidence of mutability in the coding domain (approximately 1:100 nucleotides) is exceedingly high. The different BCHE variants were in most cases identified by the analysis of sequences originating from individuals expressing a variant phenotype and not by a random screening of the population. Several of the variants (e.g. D70G) were simultaneously discovered in two continents, while many others were detected only once, an "orphan" allele.

One major physiological role of BuChE is thought to be as a scavenger of anti-ChE agents, thus protecting from inactivation the AChE of neuromuscular junctions and other cholinergic sites (Neville et al., 1990a,b). This is deduced from the fact that BuChE interacts with a wider range of anti-ChE agents (Soreq et al., 1992) and in certain cases (e.g. DFP and many carbamates) the rate of inactivation is considerably faster than that of AChE (Loewenstein et al., 1994; Schwarz et al., 1994). Accordingly, there must be an evolutionary pressure that accounts for the need for a scavenger of anti-ChE agents. There are many natural ChE inhibitors in the environment, including glycoalkaloids present in solanaceous plants (Gnatt et al., 1994), fungal antibiotics like puromycin (Hersh, 1981) and its analogs, cocaine derivatives (Gatley, 1991), poisons from several species, like oysters (Abramson et al., 1989), OPs from cyanobacteria (Carmichael, 1994), and polypeptides from snakes (fasciculin, Karlsson et al., 1985) that are offensive or defensive weapon systems, metals (aluminum, scandium and yttrium, Marquis and Lerrick, 1982), and the carbamate of calabar beans, physostigmine (Taylor, 1990). Some of these above ChE inhibitors are extremely poisonous. Several snake venoms contain peptides of 51–59 amino acid residues (e.g. fasciculin) that bind to AChE with Kd values as low as $10^{-10}$ M (Cervenansky et al., 1990; Marchot et al., 1993). However, it is perhaps significant that it is only the glycoalkaloids of the solanaceous food plants (tomato, potato, eggplant) that are inhibitors of both AChE and BuChE. Also, the uneven natural geographic distribution of these food plants must be seen alongside the large series of naturally occurring BuChE variants, also unevenly distributed among different populations—the "atypical" BuChE mutation, $D^{70}G$ (heterozygote frequency <5% among Europeans and Americans and up to 11% of other groups; (Ehrlich et al., 1994a)—with variable affinities for them. Of all the classes of natural inhibitors of the ChEs, it seems that only for the glycoalkaloids may BuChE be imagined to have adapted as a scavenger.

The "atypical" mutation also confers resistance to inhibitors of pharmacological interest. It is clinically characterized by the inability of the affected enzyme to hydrolyze succinyl choline and dibucaine, and, compared to the wild-type BuChE, displays a specific activity of 25% of the wild-type enzyme, and at least 10-fold higher $IC_{50}$ and $K_i$ values for bambuterol, physostigmine and echothiophate. The affinity toward ACh is drastically reduced, although the $K_m$ for BTCh (butyrylthiocholine) is unchanged (Neville et al., 1990a,b). If the mutant BuChE cannot scavenge anti-ChEs and reduce their serum levels, it will not protect synaptic AChE from their effects. The genetic variability of BuChE may well be the basis of the observed variability in the extent and intensity of responses to anti-ChE drugs.

BuChE is reported to hydrolyze heroin, which has a 4-fold higher $K_m$ for the "atypical" variant than for the usual enzyme (Lockridge et al., 1980). Clearly this has the potential for explaining variations in responses to this narcotic. BuChE hydrolyzes the methyl ester bond of cocaine and its derivatives. The local anesthetic, procaine is hydrolyzed by BuChE, but it has a 15-fold higher $K_m$ with the atypical variant than with the usual enzyme. Carriers of the atypical allele may not react substantially differently from carriers of the usual enzyme when receiving procaine i.m. as it would be exposed only minimally to BuChE. However, aspirin has a nearly 4-fold higher $K_m$ with "atypical" BuChE (Valentino et al., 1981). It acts after entering the blood stream where it is exposed to BuChE. This illustrates a potential for significant variations in response to pharmacological agents, arising from natural variations in this drug-processing enzyme.

The above also suggests that variant BuChEs will function in detoxifying cocaine and its derivatives. Cocaine addicts or those who overdoes easily on cocaine have susceptible BuChE variants while those people who do not seem to become addicted, or easily addicted, have resistant variants. Identification of the specific variant can determine the type of treatment and therapy needed for cocaine addiction.

The presence of allelic BuChEs can have an effect on the treatment of OP poisoning. Treatment of OP poisoning includes prophylactic and therapeutic approaches such as protection against the OP agent with reversible inhibitors (Wills, 1970), e.g. pyridostigmine, which protects some AChE molecules from inactivation by the OP agent, allowing time for spontaneously regenerating free active enzyme. Muscarinic symptoms, e.g. increased tracheobronchial and salivary secretion, can be effectively antagonized by a sufficient dosage of atropine, an antagonist of the muscarinic receptor (mAChR), while it has virtually no effect on peripheral neuromuscular activation and subsequent paralysis. The catalytically inactive phosphoryl-enzyme can be reactivated by a cationic oxime through nucleophilic displacement of the phosphoryl moiety from the active site serine (Aldridge and Reiner, 1972). Since reactivation by oximes is most marked at the skeletal neuromuscular junctions, it is an important complement to atropine therapy. These beneficial effects are less evident at autosomal effector sites and insignificant in the CNS. 2-PAM is such an oxime, with features of ACh that permit it to bind to the active site of ChEs.

An experimental approach for treatment has been to test the use of isolated human BuChE, the most prevalent soluble circulating ChE (Ashani et al., 1991; Raveh et al., 1993), as a protective agent for mice and rats. In primates, BuChE from bovine fetal or equine serum (Doctor et al. 1991; Wolfe et al., 1994; Doctor et al., 1993) has been used as a protective agent. These protocols were successful in protecting against subsequent injections of soman (an OP), preventing both acute effects, and long-term (6 weeks) behavioral effects. This approach is claimed (Wolfe et al., 1994) to be much more successful than the established alternative therapy of 2-PAM and atropine, combined with diazepam (to deal with the problem of seizures). However, the combined use of 2-PAM and human BuChE together is potentially more efficacious than either one alone, since phosphoryl-BuChE is rapidly reactivated by 2-PAM, effectively allowing BuChE to catalytically turnover OPs (Schwarz et al., 1994).

It is known that horse serum BuChE, like "atypical" human BuChE, will not hydrolyze succinyl choline (Ehrlich et al., 1994a). The oxime, 2-PAM, reactivates DFP-inactivated $D^{70}G$ BuChE at a 5-fold lower rate than does wild type BuChE. Variants having this mutation in tandem with one or two additional natural mutations (Yll4H and S425P) display a rate of reactivation as much as 40-fold lower. Thus, the well established therapy of treating OP-intoxicated patients with 2-PAM (2-pyridine aldoxime methiodide), intended to regenerate active ChE, is less efficient in the case of carriers of variant BuChE as shown in Example 2 herein below. In support of this finding, it has been reported that the response of OP-poisoned patients to 2-PAM therapy varies widely (Willems et al., 1993).

The most frequent variant, "atypical" BuChE, was compared to the common human BuChE and ACHE in its inhibition rate with several anti-ChEs of pharmacological interest (Loewenstein et al., 1994) in Example 1, herein below. With common BuChE, the carbamates physostigmine, heptyl-physostigmine (Modulanum®) and SDZ ENA 713 had inactivation rates higher than or equal to ACHE, but "atypical" BuChE had considerably lower rates. This suggests that BuChE usually reacts with the drugs in preference to AChE. However, heterozygous, and especially homozygous individuals carrying the atypical gene may well show increased sensitivity to the drugs. Moreover, the reversible inhibitor, THA, had a 300-fold higher $IC_{50}$ value with "atypical" than with common BuChE. These findings may help explain the variations in response to anti-cholinesterase therapy that have been noted, particularly in AD.

The plethora of mutations in the BCHE gene may be taken as further support for the idea that the major role of BuChE is to function as a scavenger, as the selection of proteins with modified properties will confer better resistance to specific cholinergic poisons. It may also be that the role of scavenger can conflict with another role for BuChE, for instance as a cell membrane element involved in development. In that case, a decreased affinity for an inhibitor in the environment may confer a selection advantage (Ehrlich et al., 1994a).

The recent administration of pyridostigmine bromide to over 400,000 Gulf War soldiers was probably the largest scale ever use of an experimental drug, approved only because of the anticipated exposure of those soldiers to nerve agents (Gavageran, 1994). Previous clinical studies with this drug on healthy volunteers had been limited to small numbers of healthy males and to only several days exposure. Moreover, volunteers who suffered side effects were immediately withdrawn from those studies (see, for example, Glickson et al., 1991). Thus, the Gulf War presents the first real-life experience with this anti-ChE. The war conditions included concurrent exposure to insecticides, chiefly organophosphorus anti-ChEs (Ember, 1994), which increased the level of ChE inhibition in these soldiers to an unknown extent. Adding to the exposure was the insect repellent, DEET, which has been shown to amplify the toxicity of anti-ChEs (Gavageran, 1994). It is thus probable that the total ChE inhibition levels in these soldiers exceeded those intended even for normal individuals. In heterozygote and homozygous carriers of the "atypical" BCHE allele, the capacity of blood BuChE to interact with and detoxify part of the drug would be correspondingly lower. While heterozygotes still possess about 50% of this normal protective detoxifier, "atypical" homozygotes do not. These would hence become most vulnerable to excessive ChE inhibition under treatment by any anti-ChE drug.

Pyridostigmine is not the only anti-ChE that may provoke an adverse response, as is demonstrated by applicants' analyses of several potential drugs for treating Alzheimer's disease as shown in Example 1 herein below. These all emerged as much faster inactivators of BuChE than of AChE, suggesting that when orally administered to patients they will interact primarily with plasma BuChE, so that the clinically effective dose reaching the central nervous system depends heavily on the BCHE genotype. Even without the complication of BCHE polymorphism, BuChE levels can vary with the general state of health (Ehrlich et al., 1994a). Since Alzheimer's patients are far from being as healthy as the pyridostigmine-treated soldiers, they may present yet more drastic symptoms in response to inappropriate dosage of anti-ChEs. Moreover, these patients are usually unable to communicate their difficulties, so that discrimination between effects of the drug and symptoms of the disease depends solely on the subjective observations of a caretaker, which calls for the development of reliable blind tests as set forth in the present invention to detect such responses. With the information from the present invention, appropriate dosages of these drugs can be adjusted to match specific genotypes, for the purpose of avoiding adverse responses.

As shown in Example 2 herein below, the much faster inactivation and reactivation of BuChE than AChE suggests that in vivo, BuChE reacts faster with certain OP and oxime drugs and poisons than AChE. This is relevant to the intravenous PAM administration that is used, in conjunction with other therapies, to treat OP-intoxication (Taylor, 1990). Serum PAM levels that are achieved during therapy for OP poisoning do not exceed 40 $\mu$M (Willems et al., 1993), well below its Ka. Because of the accessibility of BuChE as a serum enzyme, this raises the possibility that PAM acts by regenerating BuChE and allowing it to react with more of the OP before the OP has a chance to inactivate neuromuscular AChE, in effect turning serum BuChE into an OPase. This function appears impaired in "atypical" ($D^{70}G$) carriers, about 50% to 10% of the population (Ehrlich et al., 1994a), and in carriers of the double and triple mutations, who would therefore be expected to be poor subjects for oxime therapy for OP poisoning due to the lowered reactivation rates of their diisopropylphosphoryl- (DIP-) enzymes. As BuChE serves as a scavenger of naturally occurring ChE inhibitors (Soreq et al., 1992), this explains the recently reported variable efficacy of PAM treatment (Willems et al., 1993) and the cholinergic side-effects in Alzheimer's disease patients subjected to anti-cholinesterase therapy (Winker, 1994). In addition, Example 2 shows that, the single-step enrichment on immobilized antibody is sufficient for in-depth biochemical analysis and does not alter characteristic kinetic constants.

Cholinesterase inhibitors are primarily designed to inhibit the catalytic activity of acetylcholinesterase, which displays substrate specificity for acetylcholine. However, they frequently interact at least as effectively also with the homologous butyrylcholinesterase, which is less substrate-selective and more susceptible for inhibition by multiple inhibitors than AChE. In addition to brain, BuChE is known to be expressed in liver (Prody et al., 1987) and in the hematopoietic system (Patinkin et al, 1990). Moreover, the BCHE gene encoding BuChE is subject to incomplete somatic amplification (Lapidot-Lifson et al., 1989) and frequent mutability (Zakut et al., 1992) in several blood cell disorders. Furthermore, the BCHE gene maps to the 3q26 chromosomal location, which is often broken in leukemias (Ehrlich et al., 1994b). In addition, the BuChE protein is believed to act as a scavenger of various poisons targeted at acetylcholine binding proteins (Soreq et al., 1992; Loewenstein et al., 1993a). Interference with BuChE activity, an expected outcome of interaction with cholinesterase inhibitors, may hence imply adverse hematopoietic consequences.

To examine if this is the case, and if BuChE inhibition causes distinct effects from those anticipated under AChE inhibition, primary murine bone marrow cultures as an ex-vivo system in which BuChE is expressed were examined and antisense (AS) oligonucleotide inhibition was used to block such expression. These experiments as set forth in Example 3 herein below demonstrate the need in hematopoietic-associated diseases or conditions treatment that patients with varient BuChEs be identified so that they are not receiving anti-cholinesterase drugs. Further, these data indicate that patients with deficient BuChE expression and exposure through treatment or environmentally to anti-ChEs will cause hematopoietic differences in these patients.

The long-term in vivo-ex vivo stability of AS-BCHE inhibition effects in these experiments is of special interest. It indicates that AS-BCHE induced destruction of BCHEmRNA in young promegakaryocytes reduced development of these cells for at least 2 weeks and demonstrates that no feedback responses have occurred to compensate for BCHE suppression and retrieve normal production of megakaryocytes. This, in turn, suggests that individuals with the relatively abundant allelic variants of BCHE, in particular the "atypical" Asp7OGly ($D^{70}G$) substitution (Gnatt et al., 1994; Ehrlich et al., 1994a) may be particularly vulnerable to anticholinesterase therapy employed in neurodegenerative diseases. DNA tests detecting such carriers are therefore useful in predicting the genetic predisposition for hematopoietic damage that may result from anticholinesterase therapy.

Like AS-BCHE, the parallel AS-oligo blocking acetylcholinesterase expression (AS-ACHE) also suppresses megakaryocyte formation (Lev-Lehman et al., 1994, Soreq et al., 1994). However, unlike AS-BCHE, it also suppresses erythropoiesis ex-vivo and in vivo (Lev-Lehman et al., 1994; Soreq et al., 1994), suggesting that acetylcholinesterase participates in the erythropoietic process as well. Moreover, AS-ACHE induces a dramatic ex-vivo expansion of CFU-GEMM colony production and cell proliferation and reduces apoptosis in CFU-GEMM primary bone marrow cultures (Soreq et al., 1994). These differences reveal distinctions between the role(s) played by the two cholinesterases in mammalian hematopoiesis. Development of novel anticholinesterases should therefore take into consideration the hematopoietic involvement of the target proteins of these drugs as well as their distinct role in the hematopoietic process.

The above discussion provides a factual basis for the method of screening for a genetic based adverse predisposition to anticholinesterase therapy. The methods used with, and the utility of, the present invention can be shown by the following examples.

EXAMPLES

General Methods and Reagents:

Numbering of human BuChE residues is according to its published sequence (Prody et al, 1987). Residues can be indicated by the single letter amino acid abbreviation followed by the position generally as a superscript. Point mutations are indicated by the wild-type residue, the position in the sequence, and the mutant residue, thus, $L^{286}K$ is the replacement of leucine 286 by arginine.

Varient Enzymes:

Serum BuChE activity against BTCh was measured spectrophotometrically as detailed by Neville et al, (1990a,b; 1992). Recombinant normal and "atypical" BuChE were produced in Xenopus oocytes microinjected with in vitro transcribed BuChEmRNAs prepared from the corresponding cDNA types (Neville et al, 1990a). Alternative recombinant AChEs were produced in ACHEDNA-injected oocytes under control of the cytomegalovirus CMV promoter, using either the brain-characterixtic 3' exon 6 (Seidman et al, 1994) or the hematopoietically-expressed domain composed of the fourth pseudo-intron and the 3'-exon 5 (Karpel et al, 1994b).

Inhibitors:

Tacrine and physostigmine were purchased from Sigma Chemical Co. (St. Louis, Mo.). SDZ ENA-713 and N-heptyl physostigmine were gifts of Sandoz (Bern, Switzerland) and Merck Sharp & Dohme (Harlow, U.K.), respectively. Pyridostigmine was from Research Biochemicals International (Natik, Mass.).

Antibody Immobilizations:

Monoclonal mouse anti-human serum BuChE (No. 53-4; Gift from Dr. Nordward Petersen, Copenhegen, Denmark) or anti-human AChE (No. 101-1, 0.2 mg/ml) were absorbed to multiwell plates overnight at 4° C. in carbonate buffer (Seidman et al., 1994). Free binding sites were blocked with PBS-T buffer (144 mM NaCl, 20 mM Na phosphate pH 7.4, 0.05% Tween 20 and 0.01% Tymerosal) for 60 minutes at 37° C. (as described generally in Harlow and Lane, *Antibodies: A Laboratory Manual,* Cold Spring Harbor Laboratory, Cold Spring Harbor, N.Y., 1988.). Homogenates of microinjected oocytes or serum samples were diluted 1:20 to 1:40 in PBS-T to achieve similar activity levels and were incubated in the antibody-coated wells for four hours at room temperature with agitation, and overnight at 4° C. Plates were washed three times with PBS-T prior to use.

Inactivation and Reactivation Measurements:

Antibody-immobilized enzymes were exposed to the tested anti-ChEs in PBS-T buffer for varying times (0.5 to 80 minutes) following an initial determination of catalytic activities. At the noted time points, plates were washed three times with PBS-T and remaining substrate hydrolysis rates were determined (Loewenstein et al., 1993a). Spontaneous reactivation was measured for immobilized recombinant ChEs following complete inhibition, three washes with PBS-T, and subsequent incubation for the noted time and activity determination.

Quantitation:

To determine enzyme quantities, immobilized BuChE was incubated with a rabbit anti-human polyclonal antiserum (Dako, Glostrup, Denmark) at 1:4,000 dilution in PBS-T for 70 to 80 min at 37° C. After washing with PBS-T, horseradish peroxidase-conjugated goat-anti rabbit antibody (HRP, Jackson Laboratory, Bar Harbor, Me.) was added at 1:10,000 dilution in PBS-T. Peroxidase activity was thereafter assayed using o-phenylenediamine dihydrochloride at 1 mg/ml in phosphate/citrate buffer, pH 9.6 and Na perborate as substrates. Purified human BuChE was used for calibration, and absorbance at 45 nm was recorded on a Molecular Devices microliter plate reader.

Single-Step Enrichment for AChE or BuChE on Immobilized Antibody:

Monoclonal mouse anti-human serum BuChE (53-4) or anti-human ACHE (101-1) antibodies (Liao et al., 1993), were adsorbed to microliter plates (Nunc, Roskilde, Denmark) at 0.5 pg/ml in 0.1M carbonate buffer, pH 9.6, for at least four hours at room temperature. Plates were then washed three times in PBS-T buffer (144 mM NaCl, 20 mM Na phosphate, pH 7.4, 0.05% Tween-20). Free binding sites on the well surface of the microliter plate were blocked with PBS-T for one hour at 37° C. (as described generally in Harlow and Lane, *Antibodies: A Laboratory Manual,* Cold Spring Harbor Laboratory, Cold Spring Harbor, N.Y., 1988.). Microinjected oocyte homogenates containing the enzyme were then added at a dilution of 1:20 in PBS-T or at a concentration of 100 mIU/ml in PBS-T for at least 3 hours at room temperature with agitation. Plates were washed three times with PBS-T before use. Inactivation was performed at pH 7.4 in order to facilitate comparison with similar studies in the literature.

Measurement of Inactivation of ChEs by DFP:

Immobilised enzymes utilizing the single-step method were exposed to DFP in PBS-T buffer for varying times. Hydrolysis rates were determined in 96-well microtiter plates. To each well were added 200 $\mu$l of 30 mM butyrylthiocholine (BTCh) in 0.5 mM 3,3'-dithiobis (6-nitrobenzoic acid) (DTNB), 100 mm Na phosphate, pH 7.4. This achieved a substrate concentration at least 10 times the $K_m$ for BuChE and the natural mutants and 1.5- to 5-times that of the site-directed mutants (Gnatt et al., 1994). In the case of AChE, 2 mM acetylthiocholine was used. Absorbance at 405 nm was automatically recorded on a Molecular Devices microliter plate reader (Menlo Park, Calif., USA).

Rate of Reactivation of DIP-BuChE by PAM:

In order to minimise the extent of aging—the progressive, refractoriness of OP-inhibited enzyme to reactivation due to hydrolysis of one of the two alkyl groups on the phosphate (Taylor, 1990)—inactivations were performed at a sufficiently high DFP concentration to bring residual activities to below 2% of the uninhibited level within 10 minutes, and reactivations were begun as soon as possible, usually within 5 minutes. The wells containing the DIP-ChE (prepared utilizing the single-step method) were exposed to 1 mM PAM in PBS-T, 22° C. for various times, then washed several times with PBS-T and assayed for enzyme activity.

Example 1

Genetic and Serum Analysis

The most frequent phenotypically effective mutation of BuChE and, therefore, the most likely to be seen affecting inhibitor interactions is the substitution of aspartate at position 70 with glycine, known as the "atypical" BuChE variant (McGuire et al, 1989, Neville et al, 1990a,b, 1992). Homozygous carriers of this mutation average 1:2,500 among Caucasians (Ehrlich et al, 1994a), reaching an incidence of 1:1,000 in some sub-populations originating in the middle-East (Ehrlich et al, 1994a), which implies a frequency of approximately 3 to 7.5% heterozygotes. The frequency of this variant among Blacks is very much lower (Ehrlich et al, 1994a). The atypical variant, in contrast to the normal enzyme, was shown to be unable to hydrolyze succinylcholine, and to be much less sensitive to several inhibitors: physostigmine (Kalow & Davis) and several organophosphates, including diisopropylfluorophosphate (DFP), iso-OMPA and echothiophate (McGuire et al., 1989; Gnatt et al, 1994, Schwarz et al., 1994). Homozygous carriers of this variant allele were reported by several groups, including the applicants, to be particularly vulnerable to parathion exposure and to the use of succinylcholine at surgery, which causes in them post-anesthesia apnea (see, for example, Prody et al., 1989; reviewed by Soreq and Zakut, 1990). These would hence be logical candidates for genetic predisposition to adverse effects of anti-ChE therapies as well. Applicants learned of a family with a member (proband) who had experienced both succinylcholine-induced apnea and, during the Gulf War and under treatment with pyridostigmine, symptoms of cholinergic deficits, see following case study. The succinylcholine incident signaled a genetic variation, and applicants suspected that the adverse cholinergic symptoms reflected the patient's response to anti-ChE therapy and might well have the same genetic basis. Therefore, applicants initiated a study of the inhibitor interactions of serum ChEs from members of this family, and compared them with the enzyme from normal serum and with recombinantly produced variant ChEs.

Case Study:

H. K., born in 1970, was first referred to applicants in 1989 following an incident of two hour post-anesthesia apnea caused by succinylcholine administration in the course of knee surgery, which was treated by respiration. At the time, applicants assayed his serum BuChE against BTCh and found it to be approximately 30% of normal level and totally incapable of hydrolyzing succinylcholine, suggesting that it was the "atypical" enzyme (Neville et al., 1990a). Following both PCR amplification, informative SauIIIA restriction and direct sequencing of the corresponding region from the BCHE gene in his peripheral blood DNA by previously established techniques (Ehrlich et al., 1994a), H. K. was indeed diagnosed as being homozygous for the "atypical" allele, but not a carrier of other frequent point mutations of BuChE. The same methods revealed that both his parents and his sister are heterozygous carriers of the "atypical" BuChE allele. The patient was advised to avoid anti-ChE insecticides or drugs. H. K. served in the Israel Defense Forces in 1991, during the period of the Gulf War and, with others, received 90 mg prophylactic daily doses of pyridostigmine. He developed insomnia, weight loss and general fatigue, which worsened consistently, and a deep depression. Following discontinuation of pyridostigmine, his condition improved gradually over the following 10 weeks and H. K. is currently without symptoms.

Analysis:

To analyze on a micro scale the interactions of irreversible inhibitors with ChEs, and to enrich each of the examined CHES, applicants immobilized native human BuChEs through monoclonal antibodies to multiwell microliter plates. BuChEs from sera of individuals identified as homozygous or heterozygous carriers of the "atypical" BuChE allele were compared to those homozygous for the normal BuChE allele. For reference, applicants also immobilized recombinant Xenopus oocyte-produced variant ChEs, including normal and atypical BuChEs (Neville et al., 1992) and 3'-alternative AChEs (Karpel et al., 1994a). The enzymes immobilized in multiwell plates were subjected to successive inactivation by an anti-ChE and allowed to spontaneously reactivate. By this procedure inhibition rates could be conveniently determined, irreversible inhibitors could be removed prior to activity measurements, and amounts of the enzyme could be determined for each sample.

The specific activity of "atypical" BuChE, which cannot hydrolyze succinylcholine, was found in H. K.'s serum to be about 3-fold lower than that of the normal enzyme, which hydrolyzed 80 nmol butyrylthiocholine/min/μl serum (an average from 15 individuals), in agreement with values obtained previously for other patients homozygous for the "atypical" allele (Lockridge, 1990). Heterozygotes presented intermediate specific activities, 60–70% of normal homozygotes (average of three genetically confirmed individuals). Recombinant "atypical" and normal BuChEs confirmed his difference in specific activities (Neville et al., 1990a). Thus carriers of the "atypical" allele have a less active BuChE, although they carry amounts of serum BuChE protein similar to individuals with the normal enzyme.

Figure 1B:
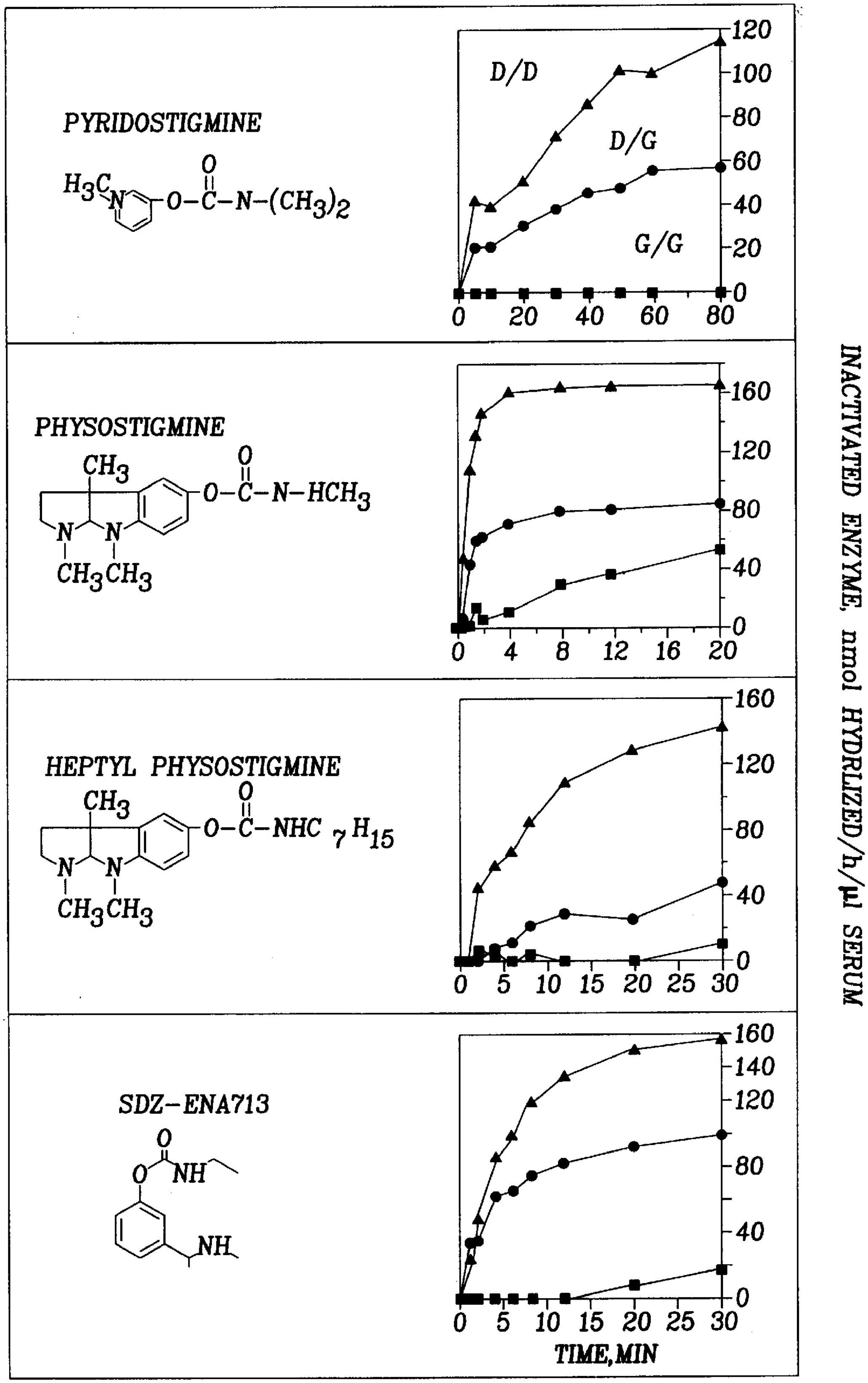

To test the interactions of "atypical" BuChE with various anti-ChEs, in 1994 applicants prepared fresh serum samples from H. K.'s peripheral blood. Serum from his heterozygous father and from genomically diagnosed normal homozygotes served for comparison. Irreversible inactivation measurements demonstrated that the "atypical" BuChE reacts with four carbamates, pyridostigmine, physostigmine, N-heptyl physostigmine and SDZ-ENA 713, much slower than its normal counterpart (FIG. 1A). Moreover, differences between the serum enzyme of the heterozygous father of the proband and homogzygous normal sera could also be discerned in the inactivation rates. Both these effects varied with the particular inhibitor being tested. For example, "atypical" BuChE displayed a decrease of about 40% in its activity when incubated with SDZ ENA 713 for 30 minutes, as compared with an 95% loss of activity in the normal enzyme at this time and with 80% in the enzyme from heterozygous serum (FIG. 1A). The loss and rate of loss of BuChE activity thus depends quite significantly on the individual's genotype. Calculations of inactivated enzyme levels reveal that the differences observed in inactivation rates reflect drastically variable capacities for scavenging each of the tested drugs in sera of patients with the normal and the atypical alleles, as displayed in FIG. 1B.

To examine whether such genetic predisposition to weakened drug interactions can also be expected for the reversible Alzheimer's disease drug, tacrine, applicants determined the $IC_{50}$ values for this drug (FIG. 2A and Table 1). To test whether the observed differences were indeed due to the examined point mutation and to mimic the heterozygote state, similar dose-dependence curves were prepared also for recombinant, Xenopus-oocyte produced normal and "atypical" monomeric BuChE and for 1:1 mixtures of the normal and the "atypical" enzyme (equal volumes of oocyte homogenates, which was close to equal amounts of the ChEs) (FIG. 2B).

In both cases, applicants observed a drastic reduction in the capacity of "atypical" BuChE as compared with the normal enzyme to interact with tacrine. Mixtures of normal and "atypical" enzyme, whether from heterozygous sera or prepared by genetic engineering, yielded the expected intermediary inhibition curves (FIG. 2B), demonstrating that these differences were not affected by multisubunit assembly and/or competition between the two types of enzyme subunits. Thus, for tacrine as well, one might expect drastically different scavenging capacities of serum BuChE depending on the genotype of the individual. For example, in the presence of 1 μm of this drug, normal BuChE would be totally inhibited whereas the "atypical" enzyme shows virtually no interaction, and sera from heterozygotes show intermediate levels of activity.

Figure 3:
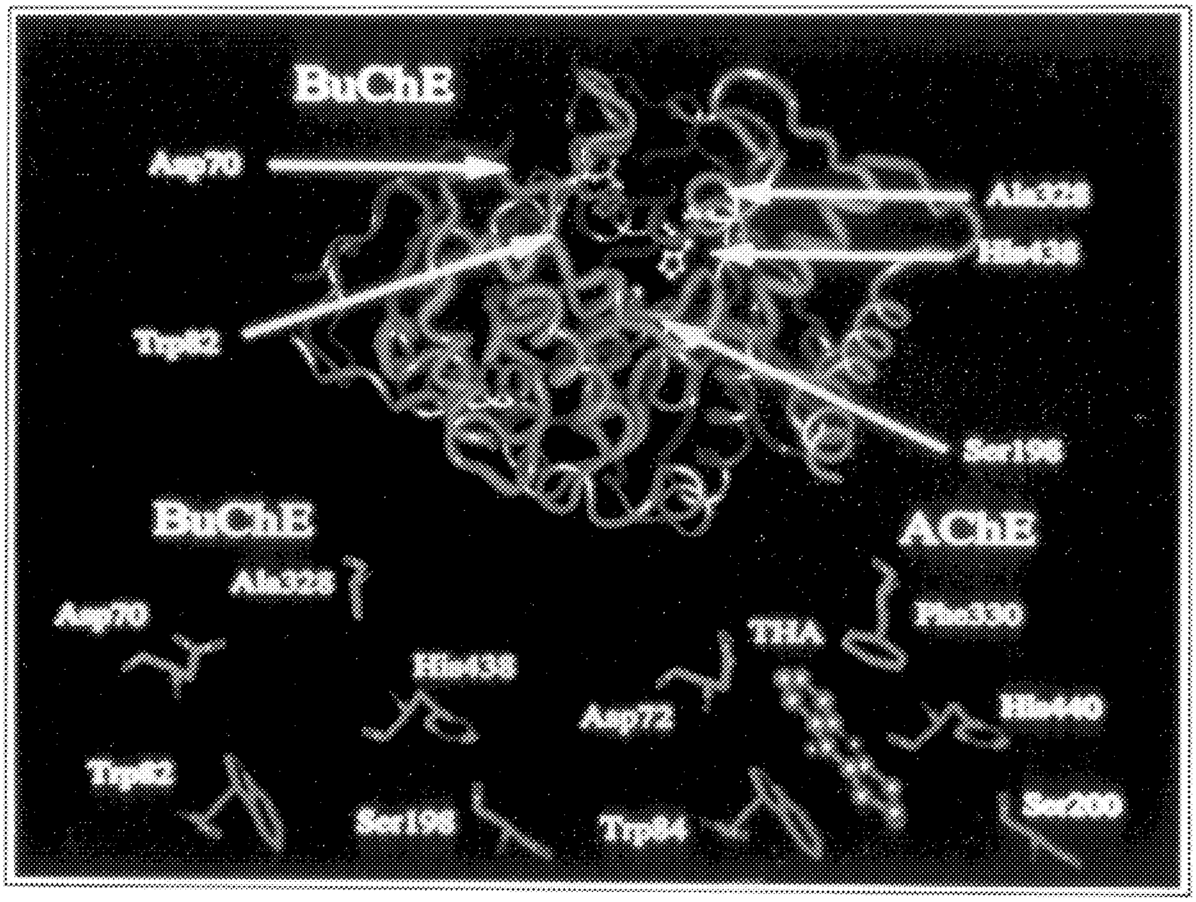
FIG. 3 is a diagram of the ChE structures and tacrine binding with the upper structure being a three-dimensional ribbon structure of BuChE showing several residues as CPK models, the active site gorge lies in the plane of the figure with its opening at the top, the structures in the bottom of the figure correspond on the right to residues surrounding tacrine in the three-dimensional sturcture of Torpedo AChE crystals soaked with tacrine compared to the structure on the left of the homologus residues of BuChE.

To understand the origin of the differences between tacrine interactions with the normal and the "atypical" enzymes, applicants employed the crystal structure of tacrine-soaked AChE (Sussman et al., 1993) (FIG. 3, lower right), and compared it with the corresponding computer-modelled region of human BuChE (Harel et al., 1992) (FIG. 3, lower left). The expanded active site domain in these proteins indeed revealed conspicuous differences in the rim of the gorge area (FIG. 3, upper). This includes Asp7O, approximately 3.7 Å from the drug, which explains why substitution of this residue may prevent the enzyme from interacting with it. The dynamic equilibrium of drug concentrations in a patient's serum depends, in addition to inactivation and removal rates, and to general hemodynamic parameters, on the rate of reactivation of drug-enzyme complexes.

To get a more complete picture of the expected outcome of treating genetically-distinct individuals with anti-ChEs, applicants further used the antibody-immobilized recombinant enzymes to follow spontaneous rates of reactivation for each of the examined drugs (FIG. 4). These measurements revealed considerable differences between drugs and for each drug between AChE and BuChE. However, there was no dramatic difference between the C-terminal alternative forms of AChE or between normal and "atypical" BuChE in these experiments (FIG. 4). Of the examined drugs, applicants noted rapid and efficient reactivation rates for complexes of AChE with physostigmine. While ACHE reactivated up to 90% in 45 minutes, in that time normal and atypical BuChE regained only 10 to 20% of its original activity. In contrast with these fast recovery rates from physostigmine inhibition, an effect reflected in the short in vivo half life of this drug, applicants observed quite limited capacities of the N-heptyl physostigmine inhibited enzymes to regain activity. With this particular drug, normal and "atypical" BuChE were faster to reactivate, yet it could only reach 10% of its original activity by 20 minutes. N-Heptyl physostigmine inactivation of both AChE forms was yet more severe, and it could only reactivate by 5%. SDZ-ENA 713 was yet more stable in its ChE interactions, with reactivation levels for all of the examined enzymes never exceeding 8%. Finally, pyridostigmine reactivation reached 50 and 10% for AChE and BuChE, respectively (FIG. 4). Based on these cumulative experiments, applicants conclude that the different $k_1$, and $IC_{50}$ values, determined in vitro (Tables 1 and 2) should influence the fate of the drugs in patients sera in vivo.

These findings show that AChE is a relatively vulnerable target for anti-ChEs in carriers of "atypical" BuChE (up to 7.5% of some populations). These observations explain at least some of the symptoms reported recently among pyridostigmine-treated soldiers and tacrine-treated Alzheimer patients, and indicate that particular DNA and serum tests will identify individuals at risk for such responses.

Applicants' study was conducted with antibody-immobilized ChEs, which enabled them to stop the inactivation or reactivation processes at any given time, remove the inhibitors and measure remaining ChE activities for obtaining correct rates of these processes. While this approach does not take into consideration pharmacodynamics, it does provide accurate values for the target molecule, i.e. the human ChEs themselves. In previous studies, inhibition levels, but not rates were determined, and measurements were performed in the presence of the inhibitors which had changed these levels. A second major feature distinguishing this study from previous ones is the comparison to human recombinant ChEs. Inhibition observed in immobilized serum enzymes confirmed with the recombinant enzyme may with confidence be taken as a true interaction of inhibitor and enzyme.

The strength of interaction of tacrine with ChEs can be understood by reference to the crystallographic model of the enzymes (FIG. 3). Tacrine is held in the active site gorge of ACHE by interaction of its aromatic rings with the aromatic rings of Trp84. At the mouth of the active site gorge Phe330 (ACHE) or Ala328 (BuChE) encloses tacrine. The alanine residue of BuChE provides a less crowded space for tacrine than the more bulky phenylalanine of AChE, reflected tacrine's slightly smaller $IC_{50}$, 0.05 for BuChE vs. 0.15 mM for AChE. In normal BuChE, the distance from the Asp7O carboxyl group to the tacrine anilinic nitrogen is only 3.7 Å, indicating the possibilty of a salt bridge. This interaction is removed in "atypical" BuChE, reflected in a 100-fold increase in tacrine's $IC_{50}$.

Applicants' analyses predict different effects of the "atypical" genotype on individual responses to the several Alzheimer's drugs. With all of the tested carbamates, significant differences are to be expected in homozygous "atypicals", and less so in heterozygotes, due to the over 10-fold differences in the inactivation rates of normal and "atypical" BuChE by these drugs. In addition to the 0.03–0.10% homozygotes among the treated population difficulties perhaps may be predicted also for those heterozygotes suffering from liver malfunction and reduced BuChE levels from other causes. The situation would be more severe under treatment with tacrine. This drug reacts with "atypical" BuChE so much more weakly than with its normal counterpart, that the "atypical" enzyme becomes a negligible factor in its interaction. Under these circumstances, even heterozygotes might show adverse responses, as their AChE levels would be reduced because of lack of scavenger under doses that cause no reduction in homozygous normals. The reported high percentage of cholinergic deficits under tacrine treatment (up to 15%, 1994) may perhaps reflect such heterozygotes and, in addition, patients with liver malfunctions and, consequently, with low serum BuChE levels.

Example 2

Evaluation of Pam Therapy for OP Poisoning

The effect of PAM therapy on OP poisoning in BuChE variants was examined. An established therapy for OP poisoning is a combination of 2-PAM and atropine, combined with diazepam (to deal with the problem of seizures). To study the effects of variant BuChE requires an investigation of the dynamics of catalysis. This includes attraction of the ligand into the deep gorge, formation of an acyl-enzyme intermediate by displacement of the choline alkoxy group by the enzyme's active site serine hydroxyl oxygen, and hydrolysis of the acyl-enzyme (Taylor, 1990; FIG. 5). Detailed dissection of catalysis by any ChE variant would discriminate between effects on one or the other of these stages of catalysis.

The inactivation of ChEs by an organophosphate agent (OP) is analogous to the acylation step (Wilson, 1954; Taylor, 1990). Phosphorylation of the active site serine (Ordentlich et al., 1993b) is just as specific for $S^{198}$ as is the acylation stage of catalysis. Furthermore, it has the same dependence on the integrity of the catalytic triad (Ordentlich et al., 1993a). Certain steps included in the action of an oxime that displaces the phosphoryl-serine bond (Hackley et al., 1955) are similarly analogous to hydrolysis (Taylor, 1990; FIG. 5). Cleavage of the phosphoryl-ChE bond is extremely slow, making OPs hemi-substrates. Their reactivation rate can be enhanced by nucleophiles (B:) such as choline, which acts from its customary binding site. More effective nucleophiles than choline accelerate the reactivation reaction much more.

PAM is Pyridine-2-aldoxime methiodide, a most successful nucleophile (Wilson, 1954), and is a rigid zwitterionic molecule that extends from the choline-binding site and juxtaposes its nucleophilic group precisely against the phosphoryl bond, which it displaces. PAM is a competitive inhibitor of catalysis (Rosenberry, 1975), and natural substrates compete with PAM in the reactivation reaction (Liu et al., 1985). The order of effectiveness of non-assisted hydrolysis of the variety of dialkylphosphoryl-ChEs formed by a spectrum of OP agents (e.g. dimethyl>diethyl>diisopropyl) is maintained in the PAM-assisted reactivations (Taylor, 1990). This suggests that reactivation shares mechanistic characteristics with the deacylation step of catalysis.

To analyse on a micro-scale and to avoid extensive purification of each of the studied proteins, applicants immobilised recombinant Xenopus oocyte-produced variant ChEs on selective monoclonal antibodies in multi-well plates and subjected the bound enzymes to successive OP inactivation and oxime-promoted reactivation. This procedure also provided undisturbed examination of each reaction. Applicants exploited this approach by measuring major changes in rates of the reaction with an OP agent and an oxime (FIG. 5), for a large series of human ChE variants differing within the gorge lining, the acyl-binding site or the C-terminus, always by comparison to the wild-type enzyme.

Spatiotemporal Dissociation of Catalytic Steps

To address involvements of several regions of ChEs in the catalytic process, applicants focused on the gorge lining and the acyl-binding site of human BuChE, since residues in these regions differ from those in ACHE (FIG. 6). Applicants collected rate constants for each of the two recombinant human enzymes as produced in microinjected Xenopus oocytes from the corresponding cloned, in vitro transcribed mRNA (Neville et al., 1992) or cDNA (Seidman et al., 1994). Because applicants expected that variations in the C-terminus would not affect catalytic properties of the enzyme (Massoulie et al., 1993; Soreq & Zakut, 1993), applicants used their approach also to test this expectation and compare variations in different regions of these proteins. To this end applicants included products of ACHEDNA vectors that encode the major form of human AChE expressed in brain and muscle (Soreq et al., 1990), and designated E6 (exons 2, 3, 4, and 6) and the alternative, that encodes a different C-terminus and represents a variant ACHEmRNA species expressed in hematopoietic and tumor cells (E5; exons 2, 3, 4, intron 4 and exon 5) (Karpel et al., 1994a). Applicants also examined a chimera of human AChE and BuChE, in which the gorge rim, the gorge-lining, the conserved oxyanion hole and the choline-binding site of BuChE (residues 58 to 133) were substituted with the homologous peptide of AChE (Loewenstein et al., 1993a). The major difference in the chimeric enzyme is that its gorge lining is more aromatic than BuChE. Several natural mutants of recombinant human BuChE (Neville et al., 1992) and site-directed point mutations its acyl-binding site (Gnatt et al., 1994) completed this series. Table 3 lists these alterations, and FIG. 6 positions these changes on the ribbon model of human BuChE.

To examine the kinetic consequences of changing these defined regions in the enzyme for the different steps of catalysis, each of the variants was reacted with diisopropylfluorophosphonate (DFP). This was followed by regeneration of activity by PAM (FIG. 5). DFP and PAM concentrations were chosen to yield phosphorylation and reactivation half-times measured in minutes. The Xenopus oocyte-produced enzymes were enriched by adsorption onto an immobilised antibody (Seidman et al., 1994; Liao et al., 1993). ELISA measurements provided determinations of the amounts of recombinant proteins for evaluation of $k_{cat}$ values and confirmed that all of the examined proteins were produced in quantities of the same order of magnitude.

The Gorge Lining Contributes to Enzyme Phosphorylation

Figure 7B:
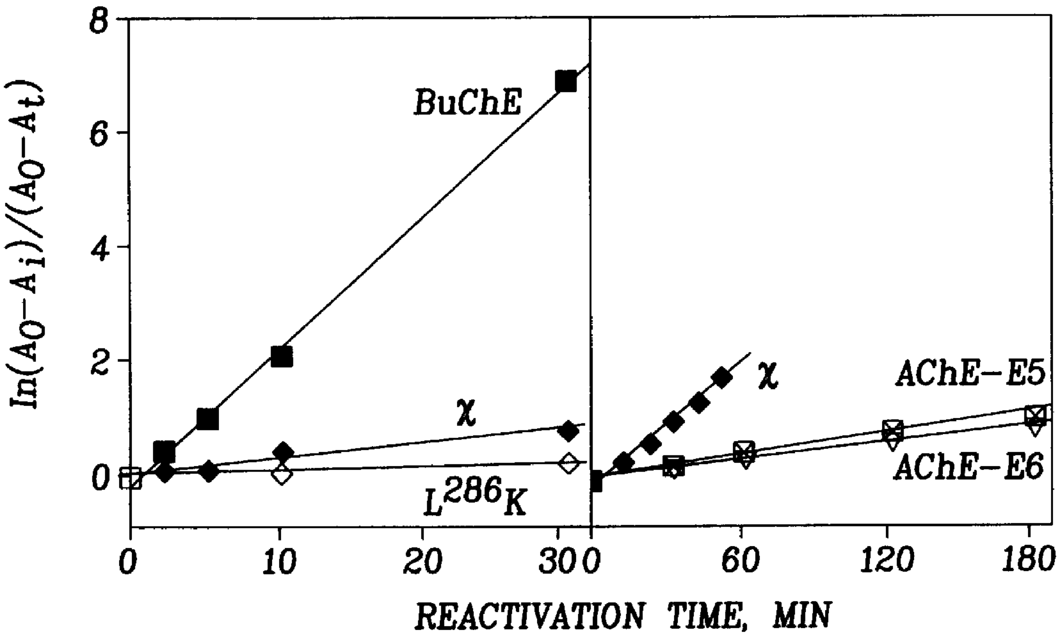

Inactivation by DFP is shown for five representative ChEs (FIG. 7A). The DFP-inactivation second order rate constant for AChE, $7\times10^4$ $min^{-1}M^{-1}$ (Table 3), was found to be 160-fold lower than that of BuChE. This value is in good agreement with the value of $3\times10^4$ $min^{-1}M^{-1}$ determined for native, purified human AChE (Main & Iverson, 1966) and is almost identical to the $9.1\times10^4$ $min^{-1}M^{-1}$ value determined more recently for purified recombinant human AChE (Ordentlich et al, 1993a). Introduction of a positive charge into the acyl-binding site in the $L^{286}K$ mutant slowed the inactivation rate of BuChE approximately 8-fold (FIG. 7A). In contrast, in-the chimera, 15 conservative and 12 non-conservative changes were sufficient to reduce the inactivation rate of BuChE 60-fold, down to the level displayed by AChE (FIG. 7B).

In general, inactivation rates of natural BuChE mutants were not severely affected. There was no effect of $D^{70}G$ or $S^{425}P$ alone, but the $D^{70}G/S^{425}P$ double mutant displayed a lowered inactivation rate that was paradoxically (and inexplicably) restored in the $D^{70}G/S^{425}P/Y^{114}H$ triple mutation. Most acyl-site mutants of $L^{286}$ and $F^{329}$ also displayed inactivation rates moderately (2- to 7-fold) lower than native BuChE, with the exception of $F^{329}Q$, which remained unchanged. Finally, both the alternative AChE forms displayed similar inactivation rates (FIG. 7A and Table 3), demonstrating, as expected, that differences in the acyl-binding site and gorge lining of ChEs contribute to the acylation rate far more than the natural variability of their C-termini.

Active Site Charges Hamper Deacylation

To study the deacylation step of catalysis, the same series of enzymes was inhibited by DFP and then assessed for rates of reactivation by PAM. The Kd for diisopropylphosphoryl-(DIP-) BuChE, 0.3 mM, is close to the value of 0.2 mM found for purified diethylphosphoryl-BuChE (Wang & Braid, 1967). Thus for this enzyme as well, the single-step enrichment on immobilized antibody is sufficient for in-depth biochemical analysis and did not alter characteristic kinetic constants.

The pseudo-first order rate constant for reactivation of DFP-inhibited BuChE (Table 3) is 25-fold higher than for either form of AChE (FIG. 7B). In contrast, the chimera displayed a reactivation rate constant only moderately (5-fold) lower than that of native BuChE. The lower rate for AChE and the chimera is attributable to a lower true first-order rate constant ($k_r$), its affinity for PAM, $K_a$, remaining unchanged (Table 4). In contrast, the BuChE $L^{286}K$ mutant displayed a 40-fold reduction in the pseudo-first order rate constant for reactivation, reflecting a reduction in both reactivation rate and affinity for PAM. Applicants further substituted an acidic, a basic, a sulphydryl and a polar group for $F^{329}$. Of these, only the sulphydryl and acidic groups disrupted the reactivation (Table 3) by 10- to 20-fold, emphasising the importance of the acyl-binding site in the reactivation process. However, altering the C-terminus of AChE affected neither the affinity for PAM nor the true first order rate constant (Table 3).

For the natural BuChE variants, effects of $D^{70}G$ and $Y^{114}H$ on reactivation are cumulative. The natural substitution of $D^{70}$ by glycine makes the resulting variant reactivate at a rate 5-fold lower than that of the wild-type enzyme. Addition of the $Y^{114}H$ or $S^{425}P$ mutation to the $D^{70}G$ mutation results in an even slower reactivating enzyme, and a combination of all three mutations in one variant causes the most severe decrease, 40-fold, in the rate of reactivation (Table 3). Thus, reactivation rates, as compared to the parent enzyme, are seriously impaired, in certain natural and site-directed mutants of BuChE, more than in the chimera. Such impairment in reactivation underlies the response to anti-cholinesterase drugs in carriers of these mutations and the need to identify them in the population.

Effects of Variations on Kcat

To compare effects on the analogous reactions with effects on catalysis, the consequences of each variation were further evaluated by determining turnover numbers. The turnover number for human BuChE as determined by applicnats, 96,000 $min^{-1}$, is in good agreement with that reported for recombinant human and mouse BuChE (Ordentlich et al., 1993a; Vellom et al., 1993). Effects on $k^{cat}$ in the various mutants are not cumulations of effects on $k_i$ and $k'_r$, nor are they expected to be, as only the slowest step is reflected in the catalytic rate. Thus, substitution of $L^{286}$ with a basic residue which affects reactivation, led to a 5-fold reduction in the turnover number (Table 3). Other replacements at this position, and substitution of the gorge lining in the chimera, had considerably smaller effects on this value.

Search for the Rate-Limiting Step of Catalysis

Figure 8:
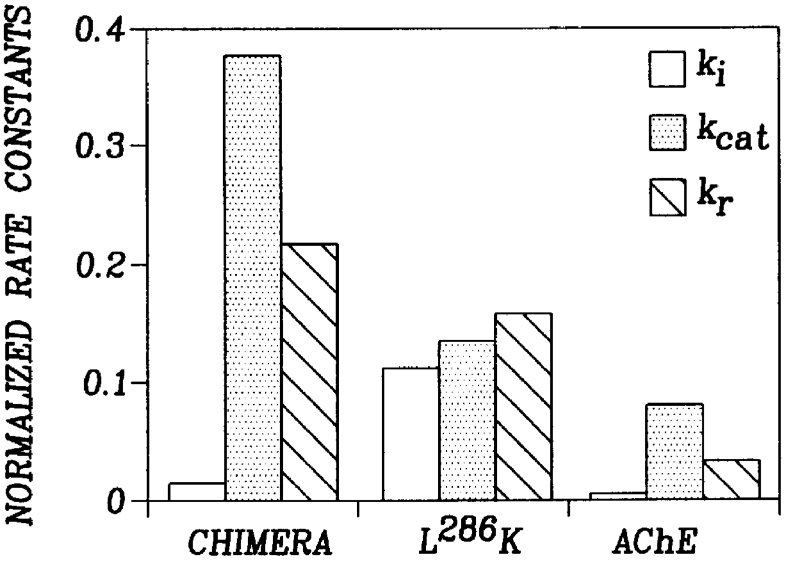
FIG. 8 is a bar graph showing tests for the rate limiting step with the open bar $k_i$, the solid dark bar $k_{cat}$, and the bar with diagonal lines $k_r$ for the chimera, $L^{286}$K mutant and AChE enzymes.

To see if conclusions could be drawn about the effect of mutations on the rate limiting step for a sampling of variants, the changes in the approach of DFP to the active site and its reaction with the active site serine (normalised $k_i$), and reaction of bound PAM with the DIP group bound to that serine (normalised $k_r$), to the overall catalytic cycle (normalised $k_{cat}$) (FIG. 8) were compaared. An OP does not interact with a ChE exactly as does a substrate, and PAM may distort the active site in ways different from binding of an acyl group. Nevertheless, the application of this approach could add another level to the conclusions that are inferred solely from consideration of the rate constants alone and shows the value of the assay for dissecting the steps of sequential reactions.

Normalised kinetic constants were used (FIG. 8): normalised $k_i$, $k_i$ (variant)/$k_i$ (BuChE) , normalised $k_r$, $k_r$ (mutant) /$k_r$ (BuChE) and normalised $k_{cat}$, $k_{cat}$ (mutant) /$k_{cat}$ (BuChE). At one extreme, one of the events leading to acylation by a variant is rate-limiting for catalysis, and the decrease from the value for BuChE in $k_{cat}$ will be in the same proportion as in $k_i$. At the other extreme, deacylation is rate-limiting and the decrease in $k_{cat}$ is in the same proportion as in $k_r$. Thus, normalised $k_r$ in one case, or normalised $k_r$, in the other, will be equal to normalised $k_{cat}$. If acylation is not rate-limiting for a variant, there is no coupling of the normalised $k_i$ with normalised $k_{cat}$; the rate-limiting step of catalysis may be seriously impaired while inactivation rate remains high (normalised $k_i$ normalised $k_{cat}$), or catalysis may remain unaffected while inactivation is impaired (normalised $k_i$<<normalised $k_{cat}$) Similarly, if deacylation is not rate-limiting, normalised $k_r$, has no relation to normalised $k_{cat}$. However, for each variant either inactivation or reactivation should track catalysis.

The test for the rate-limiting step is the near equivalency of normalised $k_{cat}$ with the normalised constant for inhibition (acylation) or for reactivation (deacylation). Inspection of FIG. 8 suggests that for the chimera and AChE using BTCh as a substrate, deacylation is rate-limiting, whereas for the $L^{286}$K variant both acylation and deacylation may be rate-limiting. The strikingly lower inactivation rate seen in AChE and the chimera (Table 3) can be accommodated without a great decrease in the catalytic rate, precisely because it is deacylation (reactivation), not acylation (inactivation) that is rate-limiting in these enzymes. The hindered access of BTCh to the AChE active site, due to the aromatic groups of the gorge lining of these enzymes, seems not to overshadow the decrease in deacylation rate, which is apparently rate-limiting. Rather, there has presumably been a minor realignment of the reactive groups at the active site that cleave the butyryl- and DIP-enzymes and regenerate the free enzyme. In contrast, when a basic group is substituted for $L^{286}$ at the acyl-binding site, proper orientation of the acyl group of the substrate is apparently disrupted, affecting both acylation and deacylation. Altogether, applicants' findings highlight precise alignments at the gorge lining and the active site as determining the catalytic distinctions between AChE and BuChE and exclude the C-terminus region from such involvement.

Example 3

Antisense Inhibition of BuChE Gene Expression Predicts Adverse Hematopoietic Consequences of Cholinesterase Inhibitors Antisense (AS) oligodeoxynucleotide inhibition was used to explore the hematopoietic effects of interference with butyrylcholinesterase expression. These experiments demonstrate the need in hematopoietic-associated diseases or conditions treatment that patients with varient BuChEs be identified so that they are not receiving anti-cholinesterase drugs. Further, these data indicate that patients with deficient BuChE expression and exposure through treatment or environmentally to anti-ChEs will cause hematopoietic differences in these patients.

Interference with BuChE activity, an expected outcome of interaction with cholinesterase inhibitors, suggests adverse hematopoietic consequences. To examine if this is the case, and if BuChE inhibition causes distinct effects from those anticipated under ACht inhibition, primary murine bone marrow cultures as an ex-vivo system in which BuChE is expressed were examined and antisense oligonucleotide inhibition was used to block such expression.

In primary bone marrow cell cultures interleukin 3 (IL-3) enables expansion of a small fraction of the existing pluripotent stem cells into multipotent progenitors. These can differentiate within four days into megakaryocyte colony forming units (CFU-MK) composed of megakaryocytes, granulocytes and macrophages (Metcalf, 1992). Addition of erythropoietin and transferrin to IL-3 leads, within 8–9 days, to the development of CFU-GEMM colonies composed of granulocytes, erythroid cells, megakaryocytes and macrophages (Koury and Bondurant, 1990). Therefore, CFU-MK and CFU-GEMM colony counts reflect the capacity of these cultures for expansion and survival of progenitors, whereas total cell numbers indicate proliferation rates. Finally, differential cell compositions of surviving colonies demonstrate which cell lineages developed under the experimental conditions employed and in what fractions. To investigate whether any of these parameters is affected by interfering with BCHE gene expression, applicant employed phosphorothioated antisense oligodeoxynucleotides (AS-oligos, Eckstein, 1985) targeted towards the BCHE gene. Recent reports demonstrate that AS-oligos toward several key proteins interfere with hematopoiesis ex-vivo and in vivo (Stein and Cheng, 1993; Gewirtz, 1993; Ratajczak and Gewirtz, 1994). More specifically, certain AS-oligos were shown to selectively block megakaryopoiesis. These include AS-oligos to the proto-oncogenes c-mpf (Methia et al., 1993), c-myb (Szczylik et al., 1993), bcr-abl and fos/jun (Lord et al., 1993) as well as to metabolically important enzymes such as cdc kinases (Lapidot-Lifson et al., 1992) or 5-lipoxygenase (Anderson et al., 1993). In vivo studies further demonstrated inhibition of erythropoiesis with AS-oligo to the c-kit ligand and to mixed colony stimulating factors (Pech et al., 1993).

In addressing the hematopoietic function of cholinesterases by this approach applicnats have previously shown that AS-oligos toward BCHE impair CFU-MK formation (Patinkin et al., 1990) and that the related AS-ACHE causes hematopoietic changes in vivo (Lev-Lehman et al., 1994) and ex-vivo (Soreq et al., 1994). To examine if the involvement of BCHE gene expression in megakaryopoiesis depends on erythropoietin, and to evaluate the duration of such interference, applicants extended their AS-BCHE analysis in CFU-MK to CFU-GEMM cultures and to the in vivo administration of AS-BCHE. In addition, the capacity of bone marrow-cells subjected in vivo to AS-BCHE treatment to develop ex-vivo into CFU-MK colonies was examined. The experimental findings demonstrate considerable erythropoietin-independent impairment induced by AS-BCHE over megakaryopoiesis ex-vivo and in vivo and predict hematopoietic abnormalities in individuals with suppressed BuChE or in those patients subjected to cholinesterase inhibition.

Specific Materials and Methods

Primary Bone Marrow Cell Cultures

Primary murine bone marrow of 8–12 week-old C3H/Hei mice was grown as described by Patinkin et al. (1990). For CFU-MK, $1\times10^5$ cells were seeded in LPM (Low protein medium, Biological Industries, Bet Haemek, Israel) containing 1% bovine serum albumin (BSA), $1\times10^{-4}$M thioglycerol, 10% conditioned medium from WEHI cells and 1% methyl cellulose and were incubated for four days. For CFU-GEMM, an additional $2.8\times10^{-4}$M human transferrin and 2 units/ml erythropoietin (Epo) (Terry Fox Laboratories, Vancouver, Canada) were added to cultures incubated for eight days at 5% $CO_2$ and 37° C. In liquid cultures of CFU-MK, the methyl cellulose was deleted and medium increased accordingly. oligonucleotides were added at day 0, either in totally phosphorothioated forms (Lapidot-Lifson et al., 1992) or phosphorothioated at the three 3'-terminal internucleotidic bonds to reduce cytotoxicity (Ehrlich et al., 1994b).

Differential Cell Analysis

Colonies of either CFU-MK or CFU-GEMM were cytospinned as described by Ehrlich et al. (1994b) and stained with May-Grunwald-Giemsa. Cells were characterized as megakaryocytes, macrophages, granulocytes or erythrocytes as detailed by Ehrlich et al. (1994b). From 500–1,500 cells were counted for each experimental section.

Evaluation of Apoptotic DNA Index

For apoptosis experiments, cells were grown at $1.5–2.5\times10^5$ cells/ml and peak concentrations of 5 μM AS- or S-BCHE for CFU-MK and 10 μM AS- or S-BCHE for CFU-GEMM. CFU-MK were seeded in liquid culture while CFU-GEMM were grown in methyl cellulose serum-free cultures. For DNA analysis, 1 μg of total DNA extracted from control cells or those treated with sense or antisense oligos was electrophoresed at 60 V for 1.5 hours on 1.5% agarose gels, then DNA was blotted on a nylon membrane (Zeta probe, Bio-Rad, Hercules, Calif.) and hybridized with [$^{32}$P] random primed labeled genomic mouse DNA. Exposure was for one day. Molecular size markers were electrophoresed in parallel. A ladder of oligonucleosome-sized DNA fragments reflecting apoptosis, appeared in all culture lanes and its intensity served to evaluate the apoptotic index of the corresponding cultures.

In Vivo Administration of AS-BCHE

Totally phosphorothioated oligodeoxynucleotide, AS-BCHE (5'-GACTTTGCTATGCAT-3') was intraperitoneally injected into a group of four three week old female Sabra mice to reach a final concentration of 5 μg/gr weight. The injected volume did not exceed 10 μl/gr weight. Phosphate buffered saline (PBS) was injected to control mice.

In Situ Hybridization

Bone marrow smears were prepared from adult female mice 20 days post-injection (once, with 5 μg/gr weight totally phosphorothioated AS-BCHE or with up to 10 μl/gr weight PBS). In situ hybridization on fresh bone marrow smears was performed using [$^{35}$S]-labeled in vitro transcribed RNA probes from the sense and antisense directions of BCHEcDNA essentially as described by Lev-Lehman et al. (1994). In situ hybridization results were analysed using a Nikon Microphot microscope connected through an interface to a Magiscan Image Analysis microscope controller (Applied Imaging Int. Ltd., U.K.) as detailed by Lev-Lehman et al. (1994). BCHEmRNA levels in megakaryocytes (MK) were determined as average numbers of silver grains per cell as detailed in Patinkin et al (1990).

Results

Figure 9A:
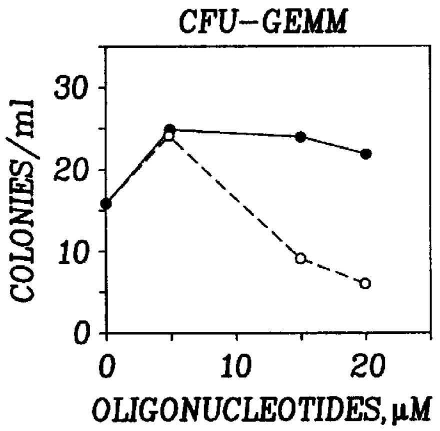
FIG. 9A–D is a series of graphs showing ex-vivo changes in colony counts and cell numbers under AS-BCHE treatment, a reproducible experiment is presented for colony counts (A,C) and cell numbers (B,D) following treatment with partially phosphorothioated oligomers, wherein -●- AS-BCHE and --○-- S-BCHE under culture conditions CFU-MK, IL-3 alone, CFU-GEMM, and IL-3 + Epo.
Figure 9B:
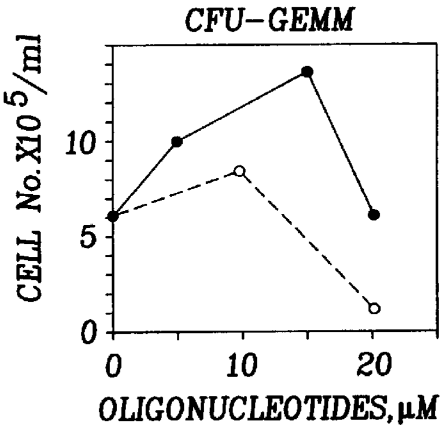
Figure 9C:
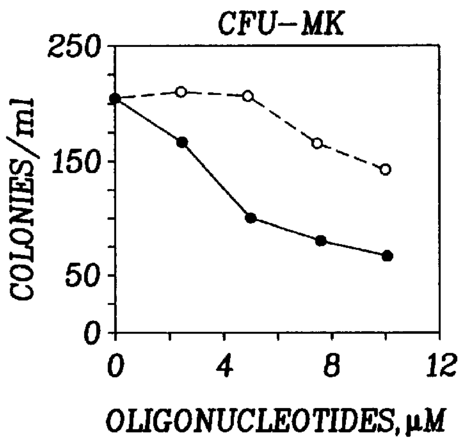

The effects of AS-BCHE treatment on primary bone marrow cell cultures containing erythropoietin were first evaluated by counting CFU-GEMM colonies. A rise of about 60% in CFU-GEMM number above control values was observed in a representative experiment shown in FIG. 9 upon application of 5 μM AS-BCHE. This colony increase was retained with rising concentration until at least 30 μM of AS-oligo (FIG. 9A and data not shown). Sense-BCHE-treated cultures exhibited a similar rise in CFU-GEMM until 5 μM concentration. However, addition of higher S-BCHE concentrations reduced colony counts down to 1/5 of control values at 20 μM oligo (FIG. 9A), demonstrating cytotoxicity. Cell counts peaked at 5–15 μM AS-BCHE with 2-fold over controls and then slowly declined, an effect which was not observed with S-BCHE which caused a significant decrease in cell counts above 10 μM (FIG. 9B). Thus, AS-BCHE did not change the number of surviving CFU-GEMM progenitors yet improved their capacity to expand in culture.

Figure 9D:
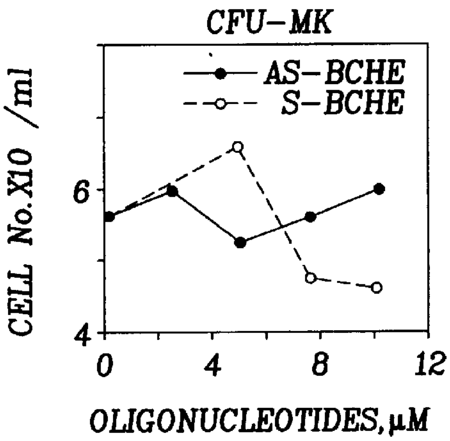

In the absence of Epo, CFU-MK numbers dropped sharply by concentrations higher than 5 μM AS-BCHE (Patinkin et al., 1990). This significant decrease in colony numbers was reproduced in this present work, using a partially phosphorothioated oligo with reduced cytotoxicity (Ehrlich et al., 1994b and FIG. 9C). Colony counts of corresponding S-BCHE treated cultures were essentially similar to those of control cultures (FIG. 9C), demonstrating the specificity of CFU-MK impairment by AS-BCHE. No significant change was observed in CFU-MK cell counts with either oligo (FIG. 9D). The AS-BCHE oligo hence suppressed CFU-MK but not CFU-GEMM colonies. In contrast, the S-BCHE oligo exerted cytotoxic effects on CFU-GEMM, but not on CFU-MK colonies, demonstrating that culture conditions affect the vulnerability of stem cells to such cytotoxicity.

The reproducibility of these oligonucleotide effects was examined by performing repetitious experiments using primary bone marrow cells from different mice (Table 5). This analysis revealed, in addition to the reduced CFU-MK counts in the presence of AS-BCHE, similar variability between experiments, from ±86.7 colonies in control cultures to ±96.7 in the presence of 15 μM AS-BCHE, in spite of the drastic reduction in mean colony counts. A significantly higher variability between CFU-MK counts occurred upon S-BCHE addition (up to ±255.0 at 15 μM oligo, $P<0.0092$). Since S-BCHE has no counterpart sequence in the cell, this change in variability probably reflects structure-related cytotoxicity particular to the S-BCHE sequence.

In contrast, the variability, but not absolute number of CFU-GEMM colony counts was reduced with addition of AS-BCHE (from ±12 in control cultures to ±6 with 30 $\mu$M AS-BCHE). However, S-BCHE did not alter the variability in CFU-GEMM counts, which remained ±10.8 in the presence of 15 $\mu$M S-BCHE (Table 5). Thus, in addition to the sequence-dependent capacity of AS-BCHE to reduce expansion of progenitor cells into CFU-MK colonies, AS-BCHE also lowered the inter-experimental variability in CFU-GEMM experiments in a sequence-dependent manner, without changing the mean colony counts.

To determine whether the administration of AS-BCHE caused non-specific changes in programmed cell death within the various cultures, yields and integrity of DNA were evaluated as detailed by Shi et al. (1992). To this end equal quantities of DNA preparations from control, AS-BCHE and S-BCHE treated cell cultures were electrophoresed, blotted and hybridized with a ($^{32}$P) -labeled probe from mouse genomic DNA. DNA from all of these cultures, either CFU-MK or CFU-GEMM, all exhibited extensive fragmentation, typical of the apoptosis expected to occur in these primary cell cultures (Shi et al., 1992; Okumura et. al., 1992). The CFU-GEMM cultures exhibited a 25% higher degree of apoptosis than did the CFU-MK cultures, possibly due to their longer incubation period (FIG. 10). However, there was no discernible difference between control lanes and AS-BCHE or S-BCHE lanes in either type of colony. Thus AS-BCHE effects in both culture types were apparently due to changes in cellular differentiation rather than associated with induction of apoptosis.

Figure 11:
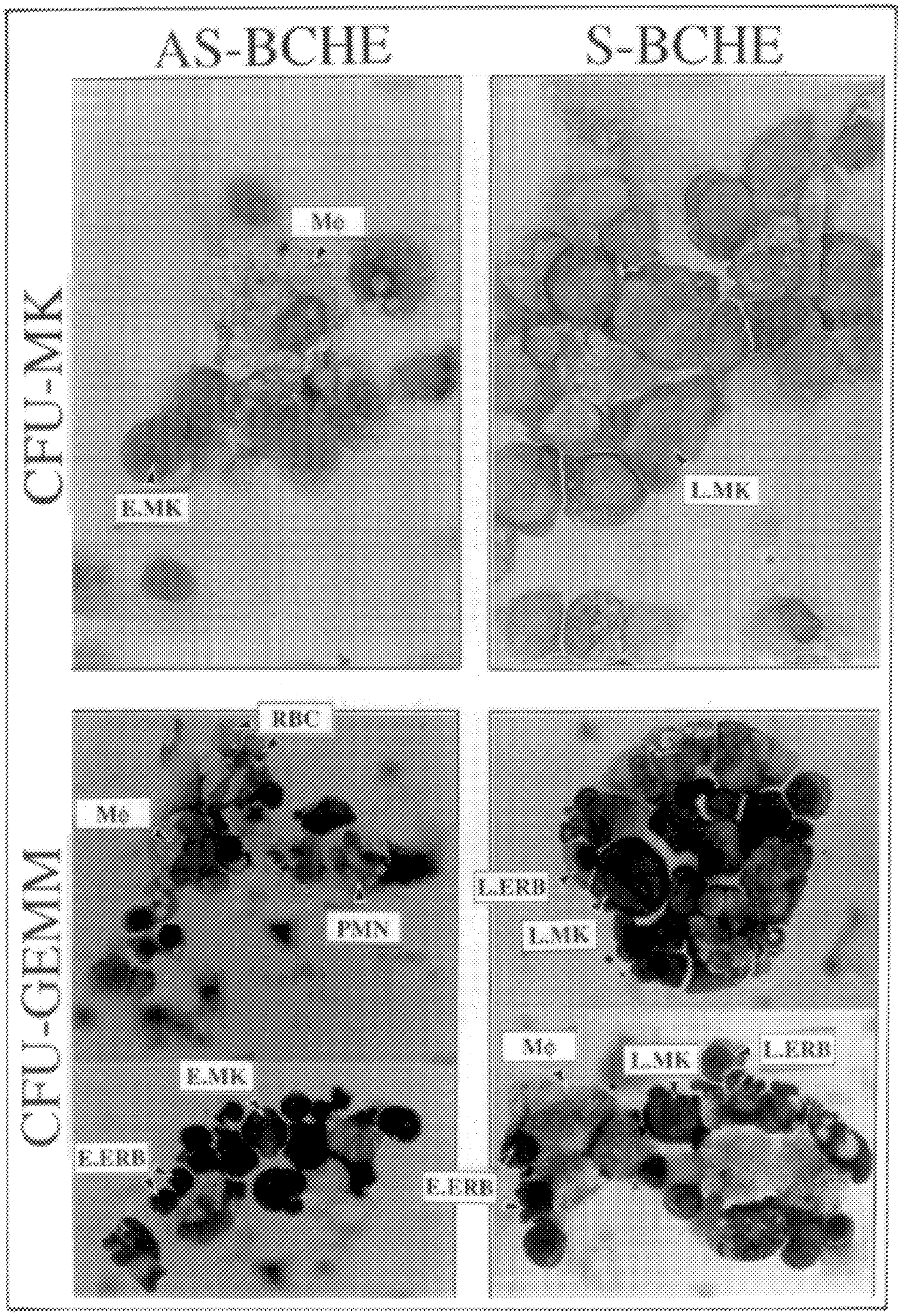
FIG. 11 is a series of photomicrographs showning AS-BCHE dependent changes in cell composition of bone marrow cultures, representative CFU-MK and CFU-GEMM cytospinned cells grown in the presence of AS-BCHE or S-BCHE are shown wherein Mø: macrophage, E.MK: Early Megakaryocyte, L.MK: Late megakaryocyte, PMN: polymorphonuclear (neutrophil), E.ERB: Early Erythroblast, L.ERB: Late Erythroblast, RBC: erythrocyte.

Colonies grown in the presence of S-BCHE included the cell types expected under the growth conditions employed. In the presence of IL-3 alone, these were primarily megakaryocytes and macrophages (FIG. 11, top panel), whereas the addition of Epo and transferrin and longer incubation times permitted erythropoiesis to occur as well (FIG. 11, bottom panel). In contrast, cultures grown with AS-BCHE included considerably less megakaryocytes and correspondingly more macrophages and neutrophils. This change was observed both in the presence of IL-3 (FIG. 11, top panel) and in the presence of IL-3 together with Epo and transferrin, (FIG. 11, bottom panel), where megakaryocytes but not erythroblasts appeared to be depleted by AS-BCHE treatment.

Figure 12A:
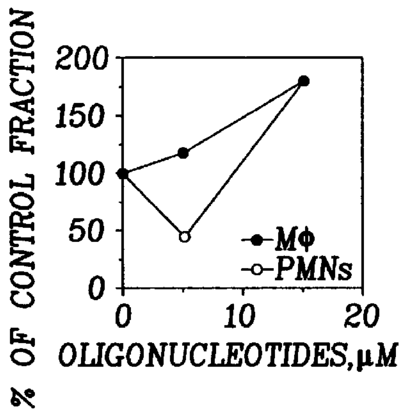
FIG. 12 is a series of graphs showing the differential compositions of AS-BCHE treated CFU-GEMM wherein Mø: -●-, E.Megs: -■-, L.Megs: -□-, PMN: -○-, E.ERB: -◆- and L.ERB: -◇-.
Figure 12B:
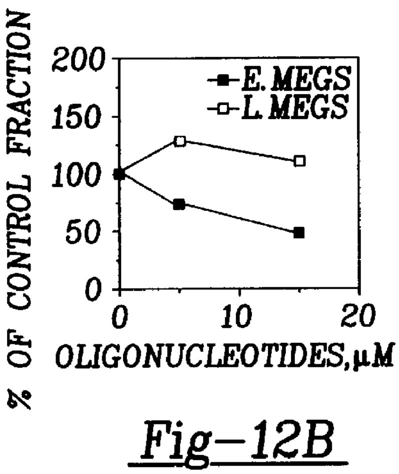

The arrest of megakaryopoiesis in CFU-MK by AS-BCHE was in line with applicants' previous findings (Patinkin et al., 1990, Lapidot-Lifson et al., 1992, Ehrlich et al., 1994b), yet the finding that it is Epo-independent was novel. To examine if this AS-BCHE-dependent interference with megakaryopoiesis reflected a significant change also in the presence of Epo, differential analysis was performed on CFU-GEMM colonies following treatment with AS-BCHE or S-BCHE. This revealed a 2-fold increase in the fractions of macrophages and neutrophils (FIG. 12A) and a corresponding decline in early, but not late MKs (FIG. 12B) with rising concentration of AS-BCHE up to 15 $\mu$M. Early and late erythroid cells exhibited little or no change in percent values (FIG. 12C), demonstrating that the erythropoietin-independent effect of AS-BCHE was limited to megakaryopoiesis and did not affect erythropoiesis in these cultures.

The duration of AS-BCHE effects in vivo was first evaluated by in situ hybridization. Twenty days following a single intraperitoneal injection of AS-BCHE, almost no BCHEmRNA could be detected over MK in bone marrow smears from treated mice (FIG. 13A). ACHEmRNA labeling of these MK was also reduced, yet to a more limited extent of 40%. Labeling decreased in both intermediary (14–20 pm diameter) and mature (>20 $\mu$m) megakaryocytes, demonstrating that cells created at or after the time of injection survived in these mice in spite of BCHEmRNA destruction in them (FIG. 13B). CFU-MK colony numbers produced ex vivo from bone marrow derived from mice injected with AS-BCHE were about 60% of those of controls, while marrow from S-BCHE-injected mice showed values slightly higher than controls (FIG. 13C). Both these results mirror exactly applicants' previously demonstrated in vitro studies (Patinkin et al., 1990, Lapidot-Lifson et al., 1992) yet extend them to reveal lowered capacity of CFU-MK progenitors subjected in vivo to AS-BCHE treatment to give rise to colonies in culture.

Discussion

The ex-vivo findings demonstrated certain enhancement in myeloid cell fractions and corresponding suppression of the megakaryocyte fractions in both CFU-MK and CFU-GEMM cultures. This erythropoietin-independent effect was sequence-dependent and not associated with general apoptotic changes. Complementary in vivo studies revealed continuation of the antisense-induced destruction of BCHEmRNA for over two weeks, no effect on megakaryocytes survival and ex-vivo suppression of CFU-MK expansion capacity following the in vivo treatment. In view of the parallel increase in cell counts in CFU-GEMM colonies, this study predicts increased myeloid cell fraction as a long-term effect of cholinesterase inhibitors blocking BuChE activity irreversibly.

To avoid non-specific cytotoxicity of the ex-vivo oligonucleotides, partial phosphorothioate protection of the relevant oligos, replacing only the three 3'-terminal internucleotidic bonds with phosphorothioate groups (Ehrlich et al., 1994b) was employed. Demonstration of a non-disturbed apoptotic index in experimental cell cultures, evidenced in unchanged ladders of fragmented DNA, indicated that the studied effects did not result from non-specific induction of programmed cell death. This, in turn, suggests that these effects were primarily due to selective destruction of the target BCHEmRNA.

In both CFU-MK and CFU-GEMM cultures, partially protected AS-BCHE but not S-BCHE enhanced myeloid and granulocyte counts while reducing the fraction of early megakaryocytes. In CFU-MK cultures, sequence-independent effects of the employed S-BCHE oligo increased the variability in colony counts; in contrast, the variability in CFU-GEMM colony counts was reduced under AS-BCHE treatment, together with suppression of megakaryocytes. These observations confirm and extend applicants previous findings (Patinkin et al., 1990, Lapidot et al., 1992, Lev-Lehman et al., 1994, Ehrlich et al., 1994b) while unexpectedly demonstrating that the hematopoietic diversion induced by AS-BCHE from megakaryopoietic toward the myeloidogenic lineages is erythropoietin-independent, involves increases in myeloid proliferation and occurs also under in vivo conditions. The occurrence of myeloid leukemia in farmers exposed to organophosphorous anticholinesterase insecticides (Brown et al., 1990) may hence be related with the "ageing" capacity of these insecticides (Soreq and Zakut, 1993), causing long-term inhibition of BuChE.

In addition, these findings demonstrate a variable sensitivity of hemopoietic progenitors of CFU-MK colonies, but not those forming CFU-GEMM to the sequence independent cytotoxicity exerted by the S-BCHE oligo. Also, these findings indicate that CFU-GEMM progenitors respond to AS-BCHE in a less variable manner than CFU-MK progenitors. Individual progenitor cells may therefore be expected to respond to specific oligos with different levels of variability, dependent both on the oligo and on the cell type.

Interestingly, the suppression of megakaryopoiesis by AS-BCHE occurred throughout the dose-response curve of CFU-GEMM and seemed to be dominant over the induction of this differentiation process by Epo (Metcalf, 1992) yet unrelated with erythropoiesis. This implies that the AS-BCHE effects are not related with the differing erythropoietin sensitivities in individual proerythroblasts (Kelly et al., 1993). Since erythroid cells and megakaryocytes are believed to stem from a common progenitor (Okumura et al., 1992), this places the function of BuChE at a later time in the megakaryopoietic pathway, after the separate commitment of these two lineages. Defects in BCHE gene expression, analogous to AS-BCHE inhibition, may therefore interfere with platelet production while enhancing myeloid cell counts.

Overexpression of hematopoietic growth factors such as IL-6 was recently shown to induce age-dependent neurodegenerative disease intransgenic mice (Campbell et al., 1993). Likewise, these current findings predict that suppression of brain enzymes like BuChE may cause adverse hematopoietic effects distinct to this particular suppression. The interrelationship between the brain and the hematopoietic system previously shown for cytokines such as LIF, (Escary et al., 1993) thus extends beyond currently known agents also into the realm of enzymes.

Throughout this application various publications are referenced by citation or number. Full citations for the publications are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

Affinity of Tacrine for ChEs: $IC_{50}$ values

| | | Recombinant | Serum |
|---|---|---|---|
| AChE | brain-type (E6) | 0.15 ± 0.08 | — |
| | hematopoietic (E5) | 0.15 ± 0.04 | — |
| BuChE | normal | 0.054 ± 0.036 | 0.082 ± 0.009 |
| | "atypical" | 11.4 ± 1.4 | 8.94 ± 2.46 |

$IC_{50}$ values for tacrine were measured for recombinant human ChEs and for sera in the presence of 1 mM butyrylthiocholine (BuChE) for 1 mM acetylthiocholine (AChE). The data shown are averages of 2 for serum samples and 3 for the recombinant enzymes.

TABLE 2

Rates of reaction of ChEs with carbamate inhibitors, second order rate constants, $k_i$ ($M^{-1}$ $min^{-1}$), for inactivation of recombinant ChEs by several carbamate inhibitors.

| | BuChE | | AChE | |
|---|---|---|---|---|
| | normal | "atypical" | E6 | E5 |
| pyridostigmine ($10^{-5}$ M) | $1.9 \times 10^3 \pm 0.2 \times 10^3$ | ND | $2.2 \times 10^4 \pm 0.9 \times 10^4$ | $2.5 \times 10^4 \pm 0.7 \times 10^4$ |
| physostigmine ($10^{-5}$ M) | $3.8 \times 10^5 \pm 1.6 \times 10^5$ | $2.6 \times 10^4 \pm 0.9 \times 10^4$ | ND | ND |
| heptyl physostigmine ($10^{-8}$ M) | $1.1 \times 10^7 \pm 0.3 \times 10^7$ | $7.7 \times 10^5 \pm 4.4 \times 10^5$ | $1.6 \times 10^6 \pm 0.7 \times 10^6$ | $1.4 \times 10^6 \pm 0.4 \times 10^6$ |
| SDZ ENA-713 ($10^{-5}$M) | $1.4 \times 10^4 \pm 0.3 \times 10^4$ | $4.7 \times 10^2 \pm 4.6 \times 10^2$ | $4.3 \times 10^3 \pm 1.8 \times 10^3$ | $3.3 \times 10^3 \pm 0.6 \times 10^3$ |

From plots such as those in FIG. 1, pseudo-first order rate constructs were calculated - slope of plot - ln(activity vs. time) then divided by the reagent concentration (in parentheses), to calculate second order rate constants. Data are averages and standard deviation of at least four determinations.
ND - Not Determined

TABLE 3

Kinetic rate constants for DFP-inactivation, PAM-reactivation and catalysis of ChEs[a]

| Variant | $k_i \times 10^{-4}$ ($M^{-1}$ $min^{-1}$) | | $k'_r \times 10^3$ ($min^{-1}$) | | $k_{cat} \times 10^{-3}$ ($min^{-1}$) |
|---|---|---|---|---|---|
| BuChE | 1220 ± 4 | (3) | 150 ± 30 | (11) | 96 ± 22 (6) |
| Chimera | 19 ± 8 | (2) | 40 ± 18 | (6) | 36 ± 14 (5) |
| AChE (E6) | 7 ± 1 | (4) | 6 ± 2 | (3) | 7.5[c] |
| AChE (E5) | 5 | (1) | 8 ± 3 | (2) | |
| $L^{286}D$ | 188 ± 24 | (3) | 120 ± 30 | (3) | 38 ± 15 (5) |
| $L^{286}Q$ | 166 ± 40 | (3) | 120 ± 20 | (4) | 42 ± 24 (5) |
| $L^{286}R$ | 268 ± 164 | (3) | 6 ± 3 | (3) | 13 ± 7 (5) |
| $L^{286}K$ | 138 ± 4 | (3) | 4 ± 1 | (3) | 13 ± 5 (4) |
| $F^{329}R$ | | | 43 | (1) | |
| $F^{329}Q$ | 1398 ± 532 | (3) | 44 ± 15 | (5) | |
| $F^{329}C$ | 552 ± 408 | (2) | 14 ± 2 | (4) | |
| $F^{329}D$ | 442 ± 190 | (3) | 8 ± 1 | (4) | |
| $S^{425}$pb | 1054 ± 408 | (3) | 134 ± 8 | (4) | |
| $D^{70}G$[b] | 1008 ± 418 | (3) | 32 ± 4 | (4) | |
| $D^{70}G + Y^{114}H$[b] | 2112 ± 1074 | (3) | 12 ± 5 | (3) | |
| $D^{70}G + S^{425}$pb | 260 ± 12 | (2) | 11 | (1) | |
| $D^{70}G + Y^{114}H + S^{425}$pb | 1598 ± 294 | (3) | 4 ± 1 | (3) | |

[a]Rate constants for inactivation ($k_i$) were calculated by linear regression analysis of $\ln(A_t)$ vs. t, where t is the time of exposure to DFP, and $A_t$ is the remaining activity at time t (e.g. FIG. 7A). Second order rate constants for inhibition ($k_i$), were calculated for each of the noted variants of human ChEs from rates observed between 1 nM and 1 μM DFP. The pseudo-first TABLE 3-continued order rate constant for reactivation, k'$_r$, was calculated by linear regression analysis of ln(A∞−A$_i$)/(A∞−A$_t$) vs. t, where t is the time of exposure to 1 mM PAM, and A∞ is the potential activity, A$_t$, the activity at time t, and A$_i$, the residual activity of the inhibited enzyme (e.g. FIG. 7B). $k_{cat}$ values were calculated from the rates of reaction of BuChE and its variants with 30 mM BTCh and the quantity of enzyme evaluated in comparison to human serum BuChE by ELISA assay of the enzyme
[b]Natural variant of BuChE. Numbers of experiments, in parentheses, and standard deviations are shown.
[c]Value form Ordentlich et al., 1993a.

TABLE 4

Constants for PAM reactivation of diisopropylphosphoryl-ChEs[a]

| Variant | $K_r \times 10^3$ (min$^{-1}$) | $K_d$ (mM) |
|---|---|---|
| BuChE | 220 ± 60 (4) | 0.30 ± 0.08 |
| Chimera | 48 ± 20 (3) | 0.34 ± 0.13 |
| AChE (E6) | 7 ± 3 (3) | 0.27 ± 0.04 |
| AChE (E5) | 10 ± 5 (2) | 0.19 ± 0.07 |
| $L^{286}K$ | 35 ± 27 (3) | >5 |

[a]True first order rate constants for reactivation ($k_r$) and dissociation constants for the DIP-enzyme/PAM complex ($K_a$) were evaluated from a plot of the reciprocals of the pseudo-first order rate constants vs. the reciprocals of PAM concentrations between 0.1 and 0.6 mM. Numbers of experiments, in parentheses, and standard deviations are shown.

AS-BCHE reduces the variability in CFU-GEMM colony counts

| | CFU-GEMM | | | CFU-MK | | |
|---|---|---|---|---|---|---|
| | Oligo [μM] | N | Colony Counts (Mean ± STD) | Oligo [μM] | N | Colony counts |
| None | 0 | 9 | 26.2 ± 12.6 | 0 | 7 | 299.3 ± 86.5 |
| AS-BCHE | 2.5 | — | — | 2.5 | 8 | 274.4 ± 111.0 |
| | 5.0 | 9 | 33.9 ± 9.8 | 5.0 | 9 | 173.4 ± 86.5 |
| | 7.5 | — | — | 7.5 | 3 | 80.7 ± 4.5 |
| | 10.0 | 5 | 32.6 ± 7.0 | 10.0 | 9 | 142.4 ± 102.2 |
| | 15.0 | 9 | 38.0 ± 16.4 | 15.0 | 5 | 130.2 ± 96.7 |
| | 20.0 | 9 | 31.0 ± 8.5 | — | — | — |
| | 30.0 | 3 | 25.7 ± 6.4 | — | — | — |
| S-BCHE | 2.5 | — | — | 2.5 | 6 | 313.5 ± 121.8 |
| | 5.0 | 2 | 38.0 ± 2.8 | 5.0 | 5 | 312.2 ± 143.2 |
| | 7.5 | — | — | 7.5 | 3 | 165.7 ± 12.7 |
| | 10.0 | 5 | 35.4 ± 10.7 | 10.0 | 7 | 231.3 ± 155.3 |
| | 15.0 | 6 | 21.5 ± 10.8 | 15.0 | 5 | 264.2 ± 255.4 |
| | 20.0 | 2 | 6.0 ± 0.0 | — | — | — |

Cell culture conditions were as detailed under Methods. The noted oligonucleotides were added at the given concentrations at day 0 and colony counts scored at the noted (N) Number of experiments on day 4 or 8 for CFU-MK and CFU-GEMM colonies, respectively. Average cell number per colony was 50 for CFU-MK and 10,000 for CFU-GEMM. Mean colony counts ± standard deviation (STD) is presented for each set of conditions.

REFERENCES

Abramson, S. N., Radic, Z., Manker, D., Faulkner, D. J. and Taylor, P. (1989) Onchidal: a naturally occurring irreversible inhibitor of acetylcholinesterase with a novel mechanism of action. Mol. Pharmacol. 36:349–354.

Aldridge, W. N. (1975) Survey of major points of interest about reactions of cholinesterases. Croatia Chim. Acta 47:225–233.

Anderson, K. M., Levin, J., Jajeh, A., Seed, T. and Harris, J. E. (1993) Induction of apoptosis in blood cells from a patient with acute myelogenous leukemia by SC41661A, a selective inhibitor of 5-lipoxygenase. Prostaglandins Leukot. Essent. Fatty Acids 4:323–326.

Arpagaus, M., Kott, M., Vatsis, K. P., Bartels, C. F. and La Du, B. N. (1990) Structure of the gene for human butyrylcholinesterase: evidence for a single copy; Biochemistry 29:124–131.

Ashani, Yi., Shapira, S., Levy, D., Wolfe, A. D., Doctor, B. P. and Raveh, L. (1991) Butyrylcholinesterase and acetylcholinesterase prophylaxis against soman poisoning in mice. Biochem. Pharmacol. 41:37–41.

Atack, J. R., Perry, E. K., Bonham, J. R., Perry, R. H., Tomlinson, B. E., Blessed, G. and Fairbairn, A. (1983). Molecular forms of acetylcholinesterase in senile dementia of Alzheimer type: selective loss of the intermediate (10S) form. Neurosci. Lett. 40:199–204.

Atack, I. R., Perry, E. K., Bonham, J. R., Candy, J. M. and Perry, R. H. (1986) Molecular forms of acetylcholinesterase and butyrylcholinesterase in the aged human central nervous system. J. Neurochem. 47:263–277.

Augustinsson, K. B. (1948) Acetylcholinesterase: a study in comparative enzymology. Acta physiol. Scand. 15 (Suppl. 52):1–182.

Balasubramanian, A. S. and Bhanumathy, C. D. (1993) Noncholinergic functions of cholinesterases. FASEB J. 7:1354–1358.

Baldessarini, R. J. (1990) Drugs and the treatment of psychiatric disorders. In: Pharmacological Basis of Therapeutics, pp. 383–435, Gilman, Rall, Nies, and Taylor (eds) Pergamon Press, New York.

Brown, L. M., Blair, A., Gibson, R., Everett, G. D., Cantor, K. P., Schiaman, L. M., Burmeister, L. F., Van Lier, S. F. and Dick, F. (1990) Pesticide exposures and other agricultural risk factors for leukemia among men in Iowa and Minnesota. Cancer Res. 50:6585–6591.

Campbell, J. L., Abraham, C. R., Mashiah, E., Kemper, P., Inglis, J. D., Oldstone, M. B. A. and Mucke, L. (1993) Neurologic disease induced in transgenic mice by cerebral overexpression of interleukin 6. Proc. Natl. Acad. Sci. USA 90:10061–10065.

Carmichael, W. W. (1994) The toxins of cyanobacteria. Sci. Amer. 270:64–72.

Cervenansky, C., Dajas, F., Harvey, A. L. and Karlsson, E. (1990) The fasciculins. In: Snake Toxins, pp. 303–321, Harvey, A. L. (ed) Pergamon Press, New York.

Clement, J. G. (1991) Hypothermia: limited tolerance to repeated soman administration and cross-tolerance to oxotremorine. Pharmacol. Biochem. Behav. 39:305–312.

Coleman et al. (1987) Interaction of a benzomorphan opiate with acetylcholinesterase and the nicotinic acetylcholine receptor. Mol. Pharm. 32:456–462.

Davis et al. (1993) Therapeutic intervention in dementia. Crit. Rev. Neurobiol. 7:41–83.

Doctor et al. (1991) Enzymes as pretreatment drugs for organophosphate toxicity. Neurosci. behav. Rev. 15:123–128.

DeKosky and Scheff (1990) Synapse loss in frontal cortex biopsies in Alzheimer's disease: correlation with cognitive severity. Ann Neurol. 27:456–464.

Dretchen et al. (1992) Protection against cocaine toxicity by human butyrylcholinesterase (BCHE) in rats (abstract). FASEB J. 6:A1282.

Eckstein, F. (1985) Nucleoside phosphorothioates. Ann. Rev. Biochem. 54:367–402.

Ember L., Chemical arms not cause of Gulf War Syndrome. Chem. Eng. News, Jul. 11, 1994; 26

Ehrlich, G., Ginzberg, D., Loewenstein, Y., Glick, D., Kerem, B., Ben-Ari, S., Zakut, H. and Soreq, H. (1994a). Population diversity and distinct haplotype frequencies associated with ACHE and BCHE genes of Israeli Jews from Trans-Caucasian Georgia and from Europe. Genomics, In press.

Ehrlich, G., Patinkin, D., Ginzberg, D., Zakut, H., Eckstein, F. and Soreq, H. (1994b) Use of partially phosphorothioated "antisense" oligodeoxynucleotides for sequence-dependent modulation of hematopoiesis. Antisense Res. and Dev., In press.

Enz et al. (1991) Pharmacologic and clinicopharmacologic properties of SDZ ENA 713, a centrally selective acetylcholinesterase inhibitor. Ann. NY Acad. Sci. 640:272–275

Enz, A., Amstutz, R., Boddeke, H. Gmelin, G. and Malanowski, J. (1993) Brain selective inhibition of acetylcholinesterase: a novel approach to therapy for Alzheimer's disease. Prog. Brain Res. 98:431–437

Escary, J. L., Perreau, J., Dumenil, D., Ezine, S. and Brulet, P. (1993). Leukemia inhibitory factor is necessary for maintenance of haematopoietic stem cells and thymocyte stimulation. Nature 363:361–364.

Foutz, A. S., Boudinot, E. and Denavit-Saubie, M. (1987). Central respiratory depression induced by acetylcholinesterase inhibition: involvement of anaesthesia. Eur. J. Pharmacol. 142:207–213.

Gatley, S. J. (1991) Activities of the enantiomers of cocaine and some related compounds as substrates and inhibitors of plasma butyrylcholinesterase. Blochem. Pharmacol. 41:1249–1254.

Gavageran, H. (1994) NIH panel rejects Persian Gulf Syndrome, Nature 369:8.

Getman, D. K., Eubanks, J. H., Camp, S., Evans, G. A. and Taylor, P. (1992) The human gene encoding acetylcholinesterase is located on the long arm of chromosome 7. Am. J. Hum. Genet. 51:170–177.

Gewirtz, A. M. (1993) Potential therapeutic applications of antisense oligodeoxynucleotides in the treatment of chronic myelogenous leukemia. Leuk. Lymphoma. 1:131–137.

Glikson et al. (1991) The influence of pyridostigmine adminstration on human neuromuscular function. Fund. Appl. Toxico. 16:288–98.

Gnatt, A., Prody, C. A., Zamir, R., Lieman-Hurwitz, J., Zakut, H. and Soreq, H. (1990). Expression of alternatively terminated unusual human butyrylcholinesterase messenger RNA transcripts, mapping to chromosome 3q26-ter, in nervous system tumors. Cancer Res. 50:1983–1987.

Gnatt, A., Ginzberg, D., Lieman-Hurwitz, J., Zamir, R., Zakut, H. and Soreq, H. (1991). Human acetylcholinesterase and butyrylcholinesterase are encoded by two distinct genes. Cell. Mol. Neurobiol. 11:91–104.

Gnatt, A., Loewenstein, Y., Yaron, A., Schwarz, M. and Soreq, H. (1994) Site-directed mutagenesis of active site residues reveals plasticity of human butyrylcholinesterase in substrate and inhibitor interactions. J. Neurochem. 62:749–755.

Goonetilleke, A., de Belleroche, J. and Guiloff, R. J. (1994) motor neurone disease. Essays Biochem. 28:27–45.

Graybiel, A. M., Pickel, V. M., Joh, T. H., Reis, D. J. and Ragsdale, C. W., Jr. (1981). Direct demonstration of a correspondence between the dopamine islands and acetylcholinesterase patches in the developing striatum. Proc. Natl. Acad. Sci. U.S.A. 78:5871–5875.

Graybiel, A. M. and Ragsdale, C. W., Jr. (1982). Pseudocholinesterase staining in the primary visual pathway of the macaque monkey. Nature 299:439–442.

Hackley, B. E. Jr., Plapinger, R., Stolberg, M. and Wagner-Jauregg, T. (1955). Acceleration of the hydrolysis of organic fluorophosphates and fluorophosphonates with hydroxamic acids. J. Am. Chem. Soc. 77:3651–3653.

Harel, M., Sussman, J. L., Krejci, E., Bon, S., Chanal, P., Massoulie, J. and Silman, I. (1992). Conversion of acetylcholinesterase to butyrylcholinesterase: modeling and mutagenesis. Proc. Natl. Acad. Sci. U.S.A. 89:10827–10831.

Harel, M., Schalk, I., Ehret-Sabatier, L., Bouet, F., Goeldner, M., Hirth, C., Axelsen, P. H., Silman, I. and Sussman, J. L. (1993) Quaternary ligand binding to aromatic residues in the active-site gorge of act acetylcholinesterase. Proc. Natl. Acad. Sci. U.S.A. 90:9031–9035.

Hersh, L. B. (1981). Inhibition of aminopeptidasd and acetylcholinesterase by puromycin and puromycin analogs. J. Neurochem. 36:1594–1596.

Isenschmid, D. S., Levine, B. S. and Caplan, Y. H. (1989) A comprehensive study of the stability of cocaine and its metabolites. J. Anal. Toxicol. 13:250–256.

Kambam, J. R., Naukam, R. and Berman, M. L. (1992) Inhibition of pseudocholinesterase activity protects from cocaine-induced cardiorespiratory toxicity in rats. J. Lab. Clin. Med. 119:553–556.

Kambam, J., Mets, B., Hickman, R. M., Janickit P., James, M. F. and Kirsch, R. E. (1993) The effects of inhibition of plasma cholinesterase and hepatic microsomal enzyme activity on cocaine, benzoylecgonine, ecgonine methyl ester, and norcocaine blood levels in pigs. J. Lab. Clin. Med. 120:323–328.

Karlsson, E., Mbugua, P. M. and Rodriguez-Ithurralde, D. (1985) Anticholinesterase toxins. Pharmacol. Ther. 30:259–276.

Karpel, R., Ben Aziz-Aloya, R., Sternfeld, M., Ehrlich, G., Ginzberg, D., Tarroni, P., Clementi, F., Zakut, H. and Soreq, H. (1994a) Expression of three alternative acetylcholinesterase messenger RNAs in human tumor cell lines of different tissue origins. Exp. Cell Res. 210:268–277.

Karpel, R., Sternfeld, M., Ginzberg, D., Guhl, E., Graessmann, A. and Soreq, H. (1994b) Overexpression of acetylcholinesterase variants induces motphogenic changes in rat glioma cells. J. Neurochem. 63 (Suppl. 1):S63D.

Kelly, L. L., Koury, M. J., Bondurant, M., Koury, S. T., Sawyer, T. and Wickrema, A. (1993) Survival or death of individual proerythroblasts results from differing erythropoietin sensitivities: A mechanism for controlled rates of erythrocyte production. Blood 82:2340–2352.

Knapp, M. J., Knopman, D. S., Solomon, P. R., Pendlebury, W. W., David, C. S., Gracon, S. I. (1994) A 30-week randomized controlled trial of high-dose tacrine in patients with Alzheimer's disease. J. Am. Med. Assn. 271:985–991.

Koury, M. J. and Bondurant, M. C. (1990) Erythropoietin retards DNA breakdown and prevents programmed death in erythroid progenitor cells. Science 248:378–381.

Lapidot-Lifson, Y., Prody, C. A., Ginzberg, D., Meytes, D., Zakut, H. and Soreq, H. (1989) Coamplification of human acetylcholinesterase and butyrylcholinesterase genes in blood cells: correlation with various leukemias and abnormal megakaryocytopoiesis. Proc. Natl. Acad. Sci. U.S.A. 86:4715–4717.

Lapidot-Lifson, Y., Patinkin, D., Prody, C. A., Ehrlich, G., Seidman, S., Ben-Aziz, R., Benseler, F., Eckstein, F., Zakut, H. and Soreq, H. (1992). Cloning and antisense oligodeoxynucleotide inhibition of a human $cdc_2$ homologue required in hematopoiesis. Proc. Natl. Acad. Sci. USA 89:579–583.

Layer, P. G. (1991). Cholinesterases during development of the avian nervous system. Cell. Mole. Neurobiol. 11:7–33.

Layer, P. G., Alber, R. and Rathjen, F. G. (1988a). Sequential activation of butyrylcholinesterase in rostral half somites and acetylcholinesterase in motoneurons and myotomes preceding growth of motor axons. Development 102:387–396.

Layer, P. G., Rommel, S., Bulthoff, H. and Hengstenberg, R. (1988b) Independent spatial waves of biochemical differentiation along the surface of chicken brain as revealed by the sequential expression of acetylcholinesterase. Cell Tissue Res. 251:587–595.

Layer, P. G., Weikert, T., Alber, R. (1993) Cholinesterases regulate neurite growth of chick nerve cells in vitro by means of a non-enzymatic mechanism. Cell Tissue Res. 273:219–226.

Lev-Lehman, E., Ginzberg, D., Hornreich, G., Ehrlich, G., Meshorer, A., Eckstein, A., Soreq, H. and Zakut, H. (1994) Antisense inhibition of acetylcholinesterase gene expression causes transient hematopoietic alterations in vivo. Gene Therapy 1:127–135.

Liao, J., Mortensen, V., Norgaard-Pedersen, B., Koch, C. and Brodbeck, U. (1993) Monoclonal antibodies against brain acetylcholinesterases which recognize the subunits bearing the hydrophobic anchor. Eur. J. Biochem. 215:333–340.

Liu, W., Zhao, K. -Y. and Tsou, C. -L. (1985). Reactivation kinetics of diethylphosphoryl acetylcholine esterase. Eur. J. Biochem. 151:525–529.

Lockridge, O. (1990). Genetic variants of human serum cholinesterase influence metabolism of the muscle relaxant succinylcholine. Pharmacol. Ther. 47:35–60.

Lockridge, O., Mottershaw-Jackson, N., Eckerson, H. W., La Du, B. N. (1980) Hydrolysis of diacetylmorphine (heroin) by human serum cholinesterase. J. Pharmac. Exp. Ther. 215:1–8.

Loewenstein, Y., Gnatt, A., Neville, L. F. and Soreq, H. (1993a) A chimeric human cholinesterase: identification of interaction sites responsible for sensitivity to acetyl- or butyrylcholinesterase-specific ligands. J. Mol. Biol. 234:289–296.

Loewenstein, Y., Denarie, M., Zakut, H. and Soreq, H. (1993b) Molecular dissection of cholinesterase domains responsible for carbamate toxicity. Chemical-Biological Interactions 87:209–216.

Loewenstein, Y., Liao, J., Norgaard-Pedersen, B., Zakut, H. and Soreq, H. (1994) Faster inhibition rates of normal BuChE as compared with AChE and the D70G "atypical" BuChE mutant predict individual variabilities in response to anticholinesterase therapy. J. Neurochem. 63 (Suppl. 1):S6D.

Lord, K. A., Abdollahi, A., Hoffman-Liebermann, B. and Liebermann, D. A. (1993) Proto-oncogenes of the fos/jun family of transcription factors are positive regulators of myeloid differentiation. Mol. Cell Biol. 13:841–851.

Main, A. R. and Iverson, F. (1966). Measurement of the affinity and phosphorylation constants governing irreversible inhibition of cholinesterases by di-isopropyl phosphofluoridate. Biochem. J. 100: 525–531.

Malinger, G., Zakut, H. and Soreq, H. (1989). Cholinoceptive properties of human primordial, preantral, and antral oocytes: In situ hybridization and biochemical evidence for expression of cholinesterase genes. J. Mol. Neurosci. 1:77–84.

Marchot, P., Khelif, A., Ji, Y. -Hi., Mansuelle, P. and Bougis, P. E. (1993) Binding of 12 $125_I$-fasciculin to rat brain acetylcholinesterase: the complex still binds diisopropyl fluorophosphate. J. Biol. Chem. 268:12458–12567.

Marquis, J. K. and Fishman, E. B. (1985). Presynaptic acetylcholinesterase. Trends Pharmacol. Sci. 6:387–388.

Marquis, J. K. and Lerrick, A. J. (1982) Noncompetitive inhibition by aluminum, scandium, and yttrium of acetylcholinesterase from Electrophorus electricus. Biochem. Pharmacol. 31:1437–1440.

Marrs, T. C. (1993) Organophosphate poisoning. Pharmac. Ther. 58:51–66.

Massoulie, J., Pezzementi, L., Bon, S., Krejci, E., Vallette, F. M. (1993) molecular and cellular biology of the cholinesterases. Prog. Neurobiol. 41:31–91.

Maulet, Y., Camp, S., Gibney, G., Rachinsky, T. L., Ekstrom, T. J. and Taylor, P. (1990) Single gene encodes glycophospholipid-anchored and asymmetric acetylcholinesterase forms: alternative coding exons contain inverted repeat sequences. Neuron 4:289–301.

McGuire, M. C. Nogueira, C. P., Bartels, C. F., Lightstone, H., Hajra, A., van der Spek, A. F. L., Lockridge, O. and La Du, B. N. (1989) Identification of the structural mutation responsible for the dibucaine-resistant (atypical) variant form of human serum cholinesterase. Proc. Natl. Acad. Sci. U.S.A. 86:953–957.

McTiernan, C., Adkins, S., Chatonnet, A., Vaughan, T. A., Bartels, C. F., Kott, M., Rosenberry, T. L., La Du, B. N. and Lockridge, O. (1987) Brain cDNA clone for human cholinesterase. Proc. Natl. Acad. Sci. U.S.A. 84:6682–6686.

McTiernan et al., (1989) Brain cNDA clone for human cholinesterase. Proc. Natl. Acad. Sci. U.S.A. 84, 6682–6686, 1987.

Metcalf, D., (1992) Hemopoietic regulators. Trends Biochem. Sci. 17:286–289.

Methia, N., Louache, F., Vainchenker, W. and Wendling, F. (1993) Oligodeoxynucleotides antisense to the proto-oncogene c-mpl specifically inhibit in vitro megakaryocytopoiesis. Blood 82:1395–1401.

Minthon, L., Gustafson, L., Dalfelt, G., Hagberg, B., Nilsson, K., Risberg, J., Rosen, I., Seiving, B. and Wendt, P. E. (1993) Oral tetrahydroaminoacridine treatment of Alzheimer's disease evaluated clinically and by regional cerebral blood flow and EEG. Dementia 4:32–42.

Neville, L. F. et al. (1990a) Aspartate-70 to glycine substitution confers resistance to naturally occurring and synthetic anionic-site ligands on in-ovo produced human butyrylcholinesterase. J. Neurosci. Res. 27:452–460.

Neville, L. F., Gnatt, A., Padan, R., Seidman, S. and Soreq, H. (1990b) Anionic site interactions in human butyrylcholinesterase disrupted by two single point mutations. J. Biol. Chem. 265:20735–20738.

Neville, L. F., Gnatt, A., Loewenstein, Y., Seidman, S., Ehrlich, G. and Soreq, H. (1992) Intramolecular relationships in cholinesterase revealed by oocyte expression of site-directed and natural variants of human BCHE. EMBO J. 11:1641–1649.

Okumura, N., Tsuji, K. and Nakahata, T. (1992) Changes in cell surface antigen expressions during proliferation and differentiation of human erythroid progenitors. Blood 80:642–650.

Olianas, M. C., Onali, P., Schwartz, J. P., Neff, N. H. and Costa, E. (1984) The muscarinic receptor adenylate cyclase complex of rat striatum: desensitization following chronic inhibition of acetylcholinesterase activity. J. Neurochem. 42:1439–1443.

Ordentlich, A., Barak, D., Kronman, C., Flashner, Y., Leitner, M., Ariel, N., Cohen, S., Velan, B. and Shafferman, A. (1993a) Dissection of the human acetylcholinesterase active center determinants of substrate specificity. Identification of residues constituting the anionic site, the hydrophobic site, and the acyl pocket. J. Biol. Chem. 268:17083–17095.

Ordentlich, A., Kronman, C., Barak, D., Stein, D., Ariel, N., Marcus, D., Velan, B., and Shafferman, A. (1993b) Engineering resistance to "aging" of phosphylated human acetylcholinesterase: role of hydrogen bond network in the active center. FEBS Lett. 334:215–220.

Ott, B. R. and Lannon, M. C. (1992) Exacerbation of parkinsonism by tacrine. Clin. Neuropharmacol. 15:322–325.

Patinkin, D., Seidman, S., Eckstein, F., Benseler, F., Zakut, H. and Soreq, H. (1990) Manipulations of cholinesterase gene expression modulate murine megakaryocytopoiesis in vitro. Mol. Cell. Biol. 10:6046–6050.

Pech, N., Hermine, O. and Goldwasser, E. (1993) Further study of internal autocrine regulation of multipotent hematopoietic cells. Blood 82:1502–1506.

Percy, M. E., Markovic, V. D., Dalton, A. J., McLachlan, D. R. C, Berg, I. M. Rusk, A. C. M., Somerville, M. J., Chodakowski, B. and Andrews, D. F. (1993) Age-associated chromosome 21 loss in Down syndrome: possible relevance to mosaicism and Alzheimer disease. Am. J. Med. Genet. 45:584–588.

Perry, E. K., Tomlinson, B. E., Blessed, G., Bergmann, K., Gibson, P. H. and Perry, R. H. (1978) Correlation of cholinergic abnormalities with senile plaques and mental test scores in senile dementia. Br. Med. J. 2:1457–1459.

Prody, C. A., Gnatt, A., Zevin-Sonkin, D., Gnatt, A., Goldberg, O. and Soreq, H. (1987) Isolation and characterization of full-length cDNA clones coding for cholinesterase from fetal human tissues. Proc. Natl. Acad. Sci. U.S.A. 84:3555–3559.

Prody, C. A., Dreyfus, P., Zamir, R., Zakut, H. and Soreq, H. (1989) De novo amplification within a "silent" human cholinesterase gene in a family subjected to prolonged exposure to organophosphorous insecticides. Proc. Natl. Acad. Sci. U.S.A. 86:690–694.

Rakonczay, Z. and Brimijoin, S. (1988) Biochemistry and pathophysiology of the molecular forms of cholinesterases. In: Subcellular Biochemistry, Vol. 12, Immunological Aspects, pp. 335–378, Harris, J. R. (ed) Plenum Press, New York.

Ratajczak, M. Z and Gewirtz, A. M. (1994) oligonucleotide-based therapies of human malignancies. In "Nucleic acids and Molecular Biology" (eds. F. Eckstein and D. J. M. Lilley) Vol. 8, Springer-Verlag, Berlin and Heidelberg, pp 298–326.

Ratner, D., Oren, B. and Vigder, K. (1983) Chronic dietary anticholinesterase poisoning. Isr. J. Med. Sci. 19:810–814.

Raveh, L., Ashani, Y., Levy, D., De La Hoz, D., Wolfe, A. D. and Doctor, B. P. (1989) Acetylcholinesterase prophylaxis against organophosphate poisoning; quantitative correlation between protection and blood-enzyme level in mice. Biochem. Pharmacol. 38:529–534.

Raveh, L., Grunwald, J., Marcus, D., Papier, Y., Cohen, E. and Ashani, Y. (1993) Human butyrylcholinesterase as a general prophylactic antidote for nerve agent toxicity; in vitro and in vivo quantitative characterization. Biochem. Pharmacol. 45:2465–2474.

Rosenberry, T. L. (1975) Acetylcholinesterase. Adv. Enzymol. 43:104–210.

Ruberg, M., Rieger, F., Villageois, A., Bonnet, A. M. and Agid, Y. (1986) Acetylcholinesterase and butyrylcholinesterase in frontal cortex and cerebrospinal fluid of demented and non-demented patients with Parkinson's Disease. Brain Res. 362:83–91.

Salte, R., Syvertsen, C., Kjonnoy, M. and Fonnum, F. (1987) Fatal acetylcholinesterase inhibition in salmonids subjected to a routine organophosphate treatment. Aquaculture 61:173–179.

Schwarz, M., Glick, D., Loewenstein, Y., Soreq, H. Engineering of human cholinesterases explains and predicts diverse consequences of administration of various drugs and poisons. Pharmacol. Therap. (in press).

Schwarz, M., Loewenstein, Y., Glick, D., Liao, J., Norgaard-Pedersen, B., Soreq, H. Catalysis by human cholinesterase variants dissected by successive organophosphorus inhibition and oxime reactivation. (Submitted for publication).

Schwarz, M., Loewenstein, Y., Glick, D., Liao, J., Norgaard-Pedersen, B. and Soreq, H. (1994) Dissection of successive organophosphorus inhibition and oxime reactivation by human cholinesterase variants. J. Neurochem. 63 (Suppl. 1):S80D.

Seidman, S., Ben Aziz-Aloya, R., Timberg, R., Loewenstein, Y., Velan, B., Shafferman, A., Liao, J., Norgaard-Pedersen, B., Brodbeck, U. and Soreq, H. (1994) Overexpressed monomeric human acetylcholinesterase induces subtle ultrastructural modifications in developing neuromuscular junctions of Xenopus laevis embryos. J. Neurochem. 62:1670–1681.

Shaw, K. P., Aracava, Y., Akaike, A., Daly, J. W., Rickett, D. L. and Albuqueruqe, E. X. (1985) The reversible cholinesterase inhibitor physostigmine has channel-blocking and agonist effects on the acetylcholine receptor-ion channel complex. Mol. Pharmacol. 28:527–538.

Shi, Y., Glynn, J. M., Guilbert, L. J., Cotter, T. G., Bissonette, R. P. and Green, D. R. (1992) Role for c-myc in activation-induced apoptotic cell death in T cell hybridomas. Science 257:212–214.

Sikorav, J. -L., Duval, N., Anselmet, A., Bon, S., Krejci, E., Legay, C., Osterlund, M., Riemund, B. and massoulie, J. (1988) Complex alternative splicing of acetylcholinesterase transcripts in Torpedo electric organ; primary structure of the precursor of the glycolipid-anchored dimeric form. EMBO J. 7:2983–2993.

Silman, I. and Futerman, A. H. (1987) Modes of attachment of acetylcholinesterase to the surface membrane. Eur. J. Biochem. 170:11–22.

Silver, A. (1974) The Biology of Cholinesterases, North-Holland Publishing Company, Amsterdam, pg.6.

Soreq, H. and Zakut, H. (1990) Cholinesterase Genes: Multilevelled Regulation, Karger, Basel.

Soreq, H. and Zakut, H. (1993) Human Cholinesterases and Anticholinesterases, Academic Press, San Diego.

Soreq, H., Ben Aziz, R., Prody, C. A., Seidman, S., Gnatt, A., Neville, L., Lieman-Hurwitz, J., Lev-Lehman, E., Ginzberg, D., Lapidot-Lifson, Y. and Zakut, H. (1990) Molecular cloning and construction of the coding region for human acetylcholinesterase reveals a G+C-rich attenuating structure. Proc. Natl. Acad. Sci. U.S.A. 87:9688–9692.

Soreq, H., Gnatt, A., Loewenstein, Y., Neville, L. F. (1992) Excavations into the active-site gorge of cholinesterases. Trends Biochem. Sci. 17:353–358.

Soreq, H., Patinkin, D., Lev-Lehman, E., Grifman, M., Ginzberg, D., Eckstein, F., and Zakut, H. (1994) Antisense oligonucleotide inhibition of acetylcholinesterase gene expression induces progenitor cell expansion and suppresses hematopoietic apoptosis ex vivo. Proc. Natl. Acad. Sci. U.S.A. (in press).

Stein, C. A. and Cheng, Y. C. (1993) Antisense oligonucleotides as therapeutic agents—Is the bullet really magical? Science 261:1004–1012.

Sussman, J. L., Harel, M., Frolow, F., Oefner, C., Goldman, A., Toker, L. and Silman, I. (1991) Atomic structure of acetylcholinesterase from Torpedo californica: a prototypic acetylcholine-binding protein. Science 253:872–879.

Sussman, J. L., Harel, M. and Silman, I. (1992) Three dimensional structure of acetylcholinesterase. In: Multidisciplinary Approaches to Cholinesterase Functions, Proceedings of the Thirty-Sixth Oholo Conference on Multidisciplinary Approaches to Cholinesterase Functions, Eilat, Israel, 6–10 Apr., 1992, pp. 95–108, Shafferman, A,, Velan, B. (eds) Plenum Press, New York.

Sussman, J. L., Harel, M. and Silman, I. (1993) Three-dimensional structure of acetylcholinesterase and its complexes with acetyllcholinesterase drugs. Chem. Bio. Interact. 87, 187–197.

Szczlik, C., Skorski, T., Ku, D. H., Nicolaides, N. C., Wen, S. C., Rudnicka, L. Bonati, A., Malaguarnera, L. and Calabretta, B. (1993) Regulation of proliferation and cytokine expression of bone marrow fibroblasts: role of c-myb. J. Exp. Med. 178:997–1005.

Taylor, P. (1990) Cholinergic agonists, Anticholinesterase agents. In: Pharmacological Basis of Therapeutics, pp. 122–130, 131–149, Gilman, A. G., Rall, T. W., Nies, A. S. and Taylor, P. (eds) Pergamon Press, New York.

Taylor, P. (1991) The cholinesterases. J. Biol. Chem. 266:4025–4028.

Taylor and Radic (1994) The cholinesterases: from genes to proteins. Annu. Rev. Pharmacol. Toxicol. 43, 281–320.

Turner, A J (1994) PIG-tailed membrane proteins. Essays Biochem. 28:113–127.

United Nations Security Council (1984) Report of specialist appointed by the Secretary General, Paper S/16433.

Valentino, R. J., Lockridge, O., Eckerson, H. W. and LaDu, B. N. (1981) Prediction of drug sensitivity in individuals with atypical cholinesterase based on in vitro biochemical studies. Biochem. Pharmacol. 30:1643–1649.

Vellom, D. C., Radic, Z., Li, Y., Pickering, N. A., Camp, S. and Taylor, P. (1993). Amino acid residues controlling acetylcholinesterase and butyrylcholinesterase specificity. Biochemistry 32:12–17.

Wang, E. I. C. and Braid, P. E. (1967) Oxime reactivation of diethylphosphoryl human serum cholinesterase. J. Biol. Chem. 242: 2683–2687.

Watkins, P. B., Zimmerman, H. J., Knapp, M. J., Gracon, S. I. and Lewis, K W. (1994) Hepatoxic effects of tacrine administration in patients with Alzheimer's disease. J. Am. Med. Assn. 271:992–998.

Weaker, L., Kiauta, T. and Dettbarn, W. -D. (1978). Relationship between acetylcholinesterase inhibition and the development of a myopathy. J. Pharmacol. Exp. Ther. 206:97–104.

Willems, J. L., DeBisschop, H. C., Verstraete, A. G., Declerck, C. Christiaens, Y. Vanscheeuwyck, P., Buylaert, W. A., Vogelaers, D. and Colardyn, F. (1993) Cholinesterase reactivation in organophosphorus poisoned patients depends on the plasma concentrations of the oxime pralidoxime methylsulphate and of the organophosphate. Arch. Toxicol. 67:79–84.

WHO (1986a) Organophosphorus Insecticides: a General Introduction. Environmental Health Criteria 63, World Health organization, Geneva.

WHO (1986b) Carbamate Pesticides: a General Introduction. Environmental Health Criteria 64, World Health Organization, Geneva.

Wills, J. H. (1970). Toxicity of anticholinesterases and treatment of poisoning. In: Anticholinesterase Agents, International Encyclopedia of Pharmacology and Therapeutics Section 13, pp. 357–369, Karczmar, A. G. (ed) Pergamon Press, Oxford.

Wilson, I. B. (1954). The mechanism of enzyme hydrolysis studied with acetylcholinesterase. In The Mechanism of Enzyme Catalysis (McElroy, W. D. & Glass, B., eds.), pp. 642–657. The Johns Hopkins Press, Baltimore.

Winker, M. A. (1994) Tacrine for Alzheimer's disease; which patient, what dose? J. Am. Med. Assn. 271:1023–1024.

Wolfe, A. D., Blick, D. W., Murphy, M. R., Miller, S. A., Gentry, M. K., Hartgraves, S. L. and Doctor, P. B. Use of cholinesterases as pretreatment drugs for the protection of rhesus monkeys against soman toxicity. Toxicol. Appl. Pharmacol. (In press)

Zakut, H., Matzkel, A., Schejter, E., Avni, A. and Soreq, H. (1985) Polymorphism of acetylcholinesterase in discrete regions of the developing human fetal brain. J. Neurochem. 45:382–389.

Zakut, H., Ehrlich, G., Ayalon, A., Prody, C. A., Malinger, G., Seidman, S., Ginzberg, D., Kehlenbach, R. and Soreq, H. (1990) Acetylcholinesterase and butyrylcholinesterase genes coamplify in primary ovarian carcinomas. J. Clin. Invest. 86:900–908.

Zakut, H., Lapidot-Lifson, Y., Leibson, R., Ballin, A. and Soreq, H. (1992). In vivo gene amplification in noncancerous cells: Cholinesterase genes and oncogenes amplify in thrombocytopenia associated with Lupus Erythematosus. Mutation Res. 276:275–284.

What is claimed is:

1. A method of screening for new adverse genetic predispositions to anticholinesterase exposure including the steps of analyzing serum from a peripheral blood sample for BuChE amount and inhibitor-susceptibilities including partially purifying serum BuChE by adsorption onto anti-BuChE-antibody-coated wells of microtiter plates and performing inhibitor-susceptibilities assays for response to an anticholinesterase exposure on the antibody-immobilized enzyme, identifying samples in which at least the BuChE amount or inhibitor-susceptibilities assay for an anticholinesterase response is below that of normal homozygous controls, and screening DNA of peripheral white blood cells from the identified blood sample differing from normal homozygous controls to identify new BuChE alleles by PCR amplification and informative SauIIIA restriction or direct sequencing wherein a new adverse genetic predisposition to anticholinesterase exposure is identified.

2. A method of screening for new protective genetic predispositions to anticholinesterase exposure including the steps of analyzing serum from a peripheral blood sample for BuChE amount and inhibitor-susceptibilities including partially purifying serum BuChE by adsorption onto anti-BuChE-antibody-coated wells of microtiter plates and performing inhibitor-susceptibilities assays for response to an anticholinesterase exposure on the antibody-immobilized enzyme, identifying samples in which one of the BuChE amount or inhibitor-susceptibilities assay for an anticholinesterase response is above that of normal homozygous controls, and screening DNA of peripheral white blood cells from the identified blood sample differing from normal homozygous controls to identify new BuChE alleles by PCR amplification and informative SauIIIA restriction or direct sequencing thereby identifying a new protective genetic predisposition to anticholinesterase exposure.

* * * * *

UNITED STATES PATENT AND TRADEMARK OFFICE

CERTIFICATE OF CORRECTION

PATENT NO. : 5,807,671
DATED : September 15, 1998
INVENTOR(S) : Soreq, et al

It is certified that error appears in the above-identified patent and that said Letters Patent is hereby corrected as shown below:

Column 1, line 8, delete "DAMD17-86-C-6010" and insert -- DAMD17-94-C-4031 --.

Signed and Sealed this

Ninth Day of March, 1999

Attest:

Q. TODD DICKINSON

Attesting Officer

*Acting Commissioner of Patents and Trademarks*